(12) United States Patent
Willner et al.

(10) Patent No.: US 9,803,233 B2
(45) Date of Patent: Oct. 31, 2017

(54) RECOGNITION-RELEASE NANOPOROUS SUBSTRATE COMPRISING ACTIVE AGENTS, METHODS OF THEIR PREPARATION AND USES

(71) Applicant: YISSUM RESEARCH DEVELOPMENT COMPANY OF THE HEBREW UNIVERSITY OF JERUSALEM LTD., Givat Ram (IL)

(72) Inventors: Itamar Willner, Mevasseret Zion (IL); Zhang Zhanxia, Jerusalem (IL); Dora Balogh, Maale Adumim (IL)

(73) Assignee: YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 14/649,998

(22) PCT Filed: Dec. 5, 2013

(86) PCT No.: PCT/IL2013/051006
§ 371 (c)(1),
(2) Date: Jun. 5, 2015

(87) PCT Pub. No.: WO2014/087410
PCT Pub. Date: Jun. 12, 2014

(65) Prior Publication Data
US 2015/0344941 A1 Dec. 3, 2015

Related U.S. Application Data

(60) Provisional application No. 61/733,611, filed on Dec. 5, 2012, provisional application No. 61/865,783, filed on Aug. 14, 2013.

(51) Int. Cl.
*C12Q 1/68* (2006.01)
*A61K 31/4745* (2006.01)
(Continued)

(52) U.S. Cl.
CPC .......... *C12Q 1/6823* (2013.01); *A61K 9/5115* (2013.01); *A61K 31/4745* (2013.01); *B82Y 15/00* (2013.01)

(58) Field of Classification Search
None
See application file for complete search history.

(56) References Cited

U.S. PATENT DOCUMENTS

2004/0076681 A1    4/2004  Dennis et al.

OTHER PUBLICATIONS

Chen et al "POlyvalent nucleic acid/mesoporous silica nanparticle conjugates: Dual stimuli-responsive vehisles for intracelular drug delivery" Angew. Chem. Int. 2011, 50: 882-886.*

(Continued)

*Primary Examiner* — Betty Forman
(74) *Attorney, Agent, or Firm* — Browdy and Neimark, PLLC

(57) ABSTRACT

The present invention relates to a porous substrate comprising at least one active agent entrapped within said pores of said substrate; wherein said pores are capped by at least one nucleic acid sequence; said agent is being released by a triggered reaction of said capping sequence with at least one analyte (biomarker) thereby allowing said capping to be cleaved from said pore. The invention further relates to methods of manufacturing said substrate, uses thereof for the controlled administration of active agents and diagnostic of conditions in a patient.

16 Claims, 14 Drawing Sheets

(51) Int. Cl.
A61K 9/51 (2006.01)
B82Y 15/00 (2011.01)

(56) References Cited

OTHER PUBLICATIONS

Zhang et al., "Biocatalytic Release of an Anticancer Drug from Nucleic-Acids-Capped Mesoporous SiO2 Using DNA or Molecular Biomarkers as Triggering Stimuli" ACS Nano, 7(10): 8455-8468 (2013).
Zhang et al., "Smart Mesoporous SiO2 Nanoparticles for the DNAzyme-Induced Multiplexed Release of Substrates" J. Am. Chem. Soc.,135:1934-1940 (2013).
Yang et al., "pH-Responsive Carrier System Based on Carboxylic Acid Modified Mesoporous Silica and Polyelectrolyte for Drug Delivery" Chem. Mater., 17:5999-6003 (2005).
Gao et al., "Synthesis, Characterization, and in Vitro pH-Controllable Drug Release from Mesoporous Silica Spheres with Switchable Gates" 26, 17133-17138 (2010).
Zheng et al., "Coordination Bonding-Based Mesoporous Silica for pH-Responsive Anticancer Drug Doxorubicin Delivery" J. Phys. Chem. 115:16803-16813 (2011).
Liu et al., "Photoregulation of Mass Transport through a Photoresponsive Azobenzene-Modified Nanoporous Membrane" Nano Lett. 4:551-554 (2004).
Aznar, et al., "Photochemical and Chemical Two-Channel Control of Functional Nanogated Hybrid Architectures**" Adv. Mater. pp. 2228-2231 (2007).
Liu et al., "Tunable Redox-Responsive Hybrid Nanogated Ensembles" J. Am. Chem. Soc. 130:14418-14419 (2008).
Luo, et al., "Mesoporous Silica Nanoparticles End-Capped with Collagen: Redox-Responsive Nanoreservoirs for Targeted Drug Delivery**"Chem. Int. Ed. 50:640-643 (2011).
Wan et al., "Fluorescent pH-Sensing Organic/Inorganic Hybrid Mesoporous Silica Nanoparticles with Tunable Redox-Responsive Release Capability" 26:15574-15579 (2010).
Yu et al., "Mesoporous Silica Particles as Templates for Preparing Enzyme-Loaded Biocompatible Microcapsules" F. Adv. Mater. 17, 1737-1741 (2005).
Park, C.; et al "Enzyme Responsive Nanocontainers with Cyclodextrin Gatekeepers and Synergistic Effects in Release of Guests" Am Chem. Soc. 131 : 16614-16615 (2009).
Lei, C.; et al "Entrapping Enzyme in a Functionalized Nanoporous Support" Am. Chem. Soc. 124: 11242-11243 (2002).
Takahashi, H.; et al "Catalytic Activity in Organic Solvents and Stability of Immobilized Enzymes Depend on the Pore Size and Surface Characteristics of Mesoporous Silica" Chem. Mater. 12 : 3301-3305. (2000).
Nguyen T. D.; et al "A reversible molecular valve" Proc. Natl. Acad. Sci. USA , 102: 10029-10034. (2005).
Nguyen T. D.; et al "Design and Optimization of Molecular Nanovalves Based on Redox-Switchable Bistable Rotaxanes" J. Am. Chem. Soc. 129, 626-634. (2007).
Li, D.; et al "Optical Analysis of Hg2+ Ions by Oligonucleotide-Gold-Nanoparticle Hybrids and DNA-Based Machines" Chem. Int. Ed. , 47 : 3927-3931. (2008).
Miyake, Y.; et al "Mercury-Mediated Formation of Thymine-Hg-Thymine Base Pairs in DNA Duplexes" J. Am. Chem. Soc. , 128 : 2172-2173. (2006).
Ono, A.; et al "Highly Selective Oligonucleotide-Based Sensor for Mercury(II) in Aqueous Solution" Chem. Int. Ed. , 43, 4300-4302. (2004).
Freeman, R.; et al "Multiplexed Analysis of Hg2+ and Ag+ Ions by Nucleic Acid Functionalized CdSe/ZnS Quantum Dots and Their Use for Logic Gate Operations" Chem. Int. Ed. 48 : 7818-7821. (2009).
Huang W. T.; et al "A reversile fluorescence nanoswitch based on bifunctional reduced graphene oxide: use for detection of Hg2+ and molecular logic gate operation" Chem. Commun. , 47 : 7800-7802. (2011).
Wang, Z.-G.; et al "All-DNA finite-stat automata with finite memory" Proc. Natl. Acad. Sci. USA , 107 : 21996-22001. (2010).
Liu, J.; et al "Functional Nucleic Acid Sensors" Chem. Rev. , 109: 1948-1998. (2009).
Tombelli, S.; et al "Analytical applications of aptamers" Biosens. Bioelectron. , 20 : 2424-2434. (2004).
Willner, I.; "Electronic Aptamer-Based Sensors" Chem. Int. Ed., 46 : 6408-6418. (2007).
Li, D.; et al "Amplified Analysis of Low-Molecular-Weight Substrates or Proteins by the Self-Assembly of SNAzyme-Aptamer Conjugates" J. Am. Chem. Soc. , 129, 5804-5805. (2007).
Niazov, T.; et al "DNAzyme-Functionalized Au Nanoparticles for the Amplified Detection of DNA or Telomerase Activity" Nano Lett., 4 : 1683-1687. (2004).
Liu, J.; et al "Accelerated Color Change of Gold Nanoparticles Assembled by DNAzymes for Simple and Fast Colorimetric Pb2+ Detection" J. Am. Chem. Soc. , 126: 12298-12305. (2004).
Liu, J. et al "A DNAzyme Catalytic Beacon Sensor for Paramagnetic Cu2+ Ions in Aqueous Solutioin with High Sensitivity and Selectivity" J. Am. Chem. Soc. , 129 : 9838-9839. (2007).
Dittmer, W. U.; et al "A DNA-Based Machine That Can Cyclically Bind and Release Thrombin" Chem. Int. Ed. , 43 : 3550-3553. (2004).
Shlyahovsky et al "Spotlighting of Cocaine by an Autonomous Aptamer-Based Machine" J. Am. Chem. Soc. , 129: 3814-3815. (2007).
Liu, Y.; et al "Aptamer-Directed Self-Assembly of Protein Arrays on a DNA Nanostructure" Chem. Int. Ed, 44 : 4333-4338. (2005).
Kang, H.; et al W. "A Surface Energy Transfer Nanoruler for Measuring Binding Site Distances on Live Cell Surfaces" Chem. Com-mun. , 46 : 249-251. (2010).
Liu, J.;et al "Quantum Dot Encoding of Aptamer-Linked Nanostructures for One-Pot Simultaneous Detection of Multiple Analytes" Anal. Chem. , 79 : 4120-4125. (2007).
Seegin, G.; "Enzyme-Free Nucleic Acid Logic Circuits" Science 314: 1585-1588. (2006).
Elbaz, J.; et al "DNA computing circuits using libraries of DNAzyme subunits" Nature Nanotech., 5 : 417-422. ( 2010).
Winfree, E. Qian, L. "Scaling Up Digital Circuit Computation with DNA Strand Displacement Cascades" Science 332: 1196-1201. (2011).
Chen, C.; et al "Stimuli-responsive controlled-release system using quadruplex DNA-capped silica nanocontainers" Nucleic Acids Res. , 39 : 1638-1644. (2011).
He, D.; et al "A Photon-Fueled Gated-Like Delivery System Using i-Motif DNA Functionalized Mesoporous Silica Nanoparticles" Adv. Funct. Mater. , DOI: 10.1002/adfm.201201343 (2012).
Zhang, Y.; et al "DNA-capped mesoporous silica nanoparticles as an ion-responsive release system to determine the presence of mercury in aqueous solutions" Anal. Chem. , 84 : 1956-1962. (2012).
Yongqiang Wen et al, "DNA-Baded intelligent logic controlled release systems" XP055106438, 48 (67) Jan. 1, 2012.
Xiaoxiao He et al, "ATP-Responsive Controll Release System Using Aptamer-Functionalized Mesoporous Silica Nanoparticles" XP055106436, .28 (35), Sep. 4, 2012.
Yunfei Zhang et al, "DNA-Capped Mesoporous Silica Nanoparticles as an Ion-Responsive Release System to Determine the Presence of Mercury in Aqueous Solution" XP055106443, .84, (4), Feb. 21, 2012.
Yufang Zhu et al, "Cytosine-phosphodiester-guanine oligodeoxynucleotide (CpG ODN0-capped hollow mesoporous silica particles for enzyme-triggered drug delivery" XP055106446, 40 (39), Jan. 1, 2011.
Zhanxia Zhang et al, "Smart Mesoporous SiO2 Nanoparticles for the DNAzyme-Induced Multiplexed Release of Substrates" XP055106464, 135 (5), Feb. 6, 2013.

(56) References Cited

OTHER PUBLICATIONS

Zhanxia Zhang et al, "Biocatalytic Release of an Anticancer Drug from Nucleic-Acids-Capped Mesoporous SiO2 Using DNA or Molecular Biomarkers as Triggering Stimuli" XP055106465, 7 (10), Oct. 22, 2013.

Patel, et al., Enzyme-Responsive Snap-Top Covered Silica Nanocontainers, J. Am. Chem. Soc., 2008, pp. 2382-2382, vol. 130, No. 8.

\* cited by examiner

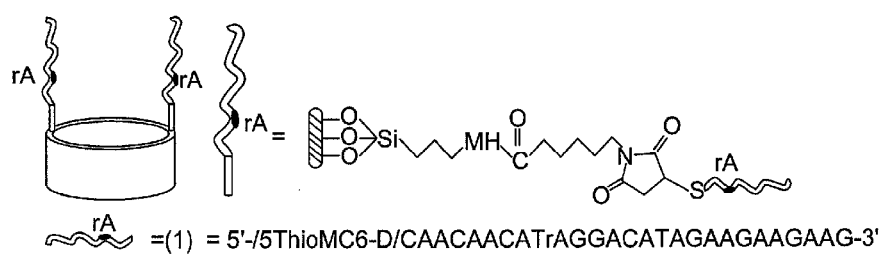
Fig. 1A
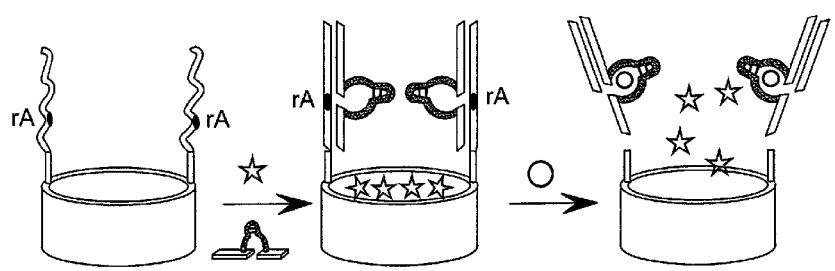
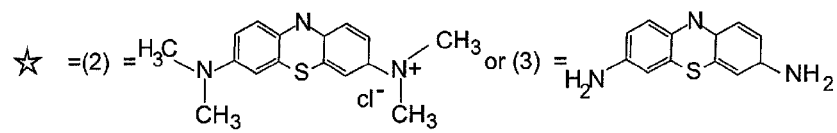
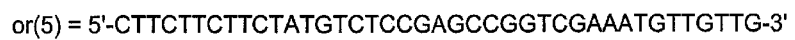

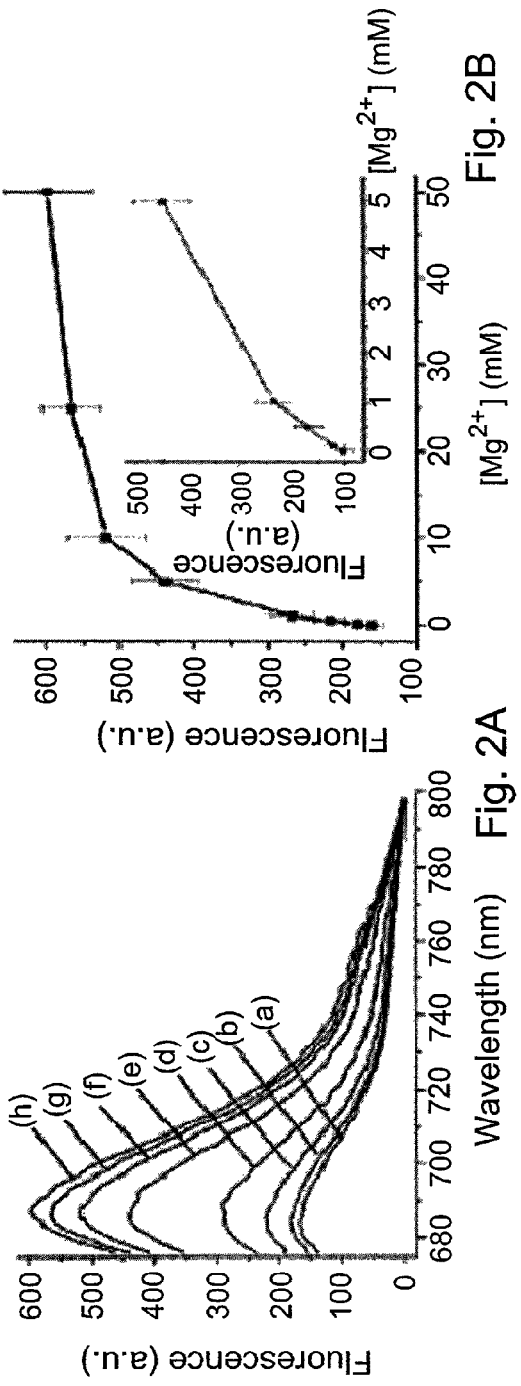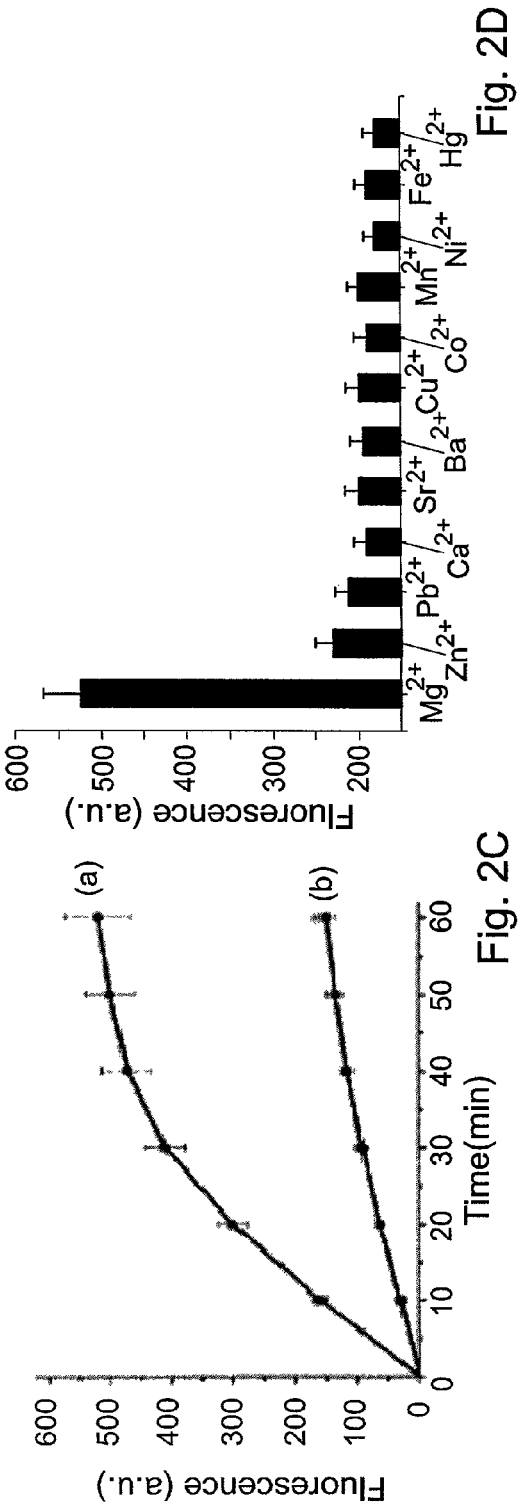

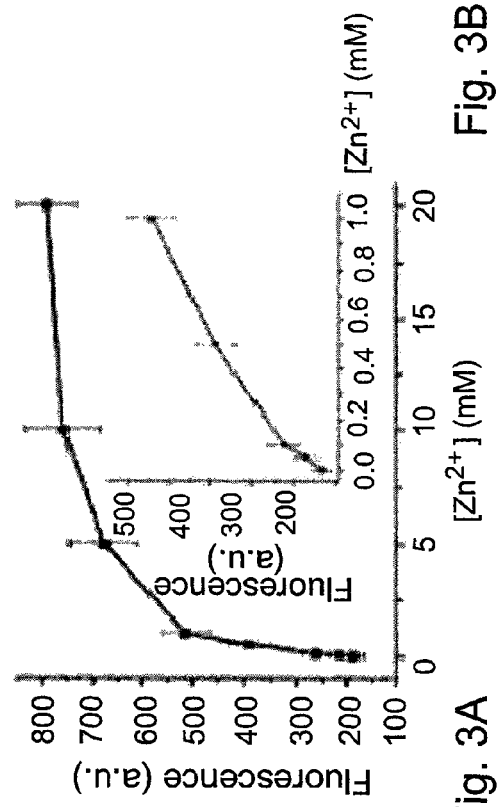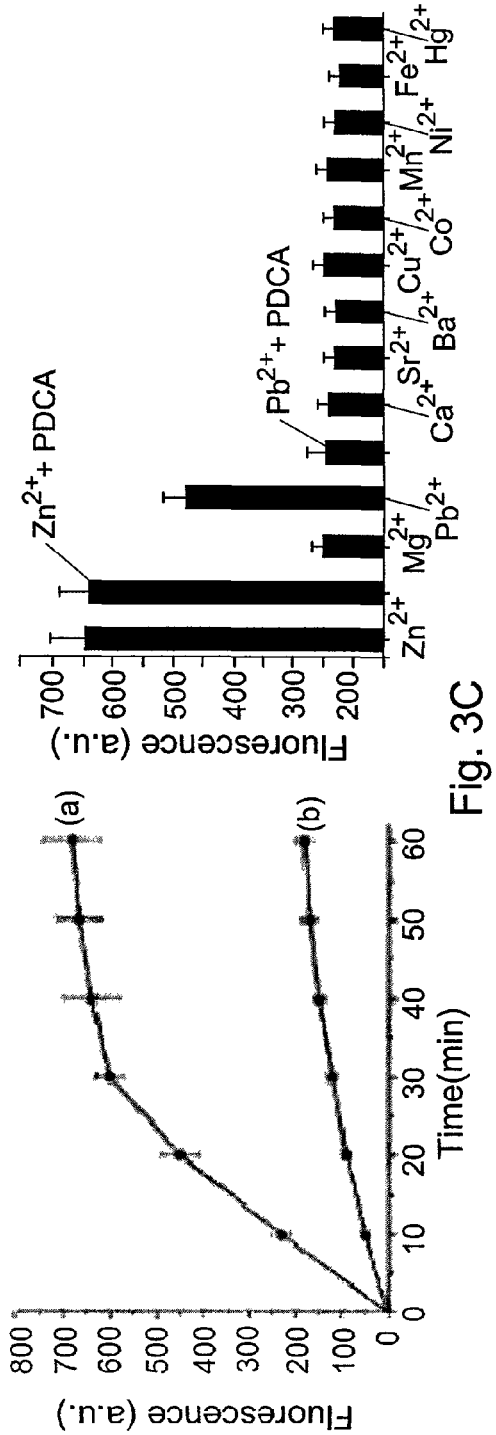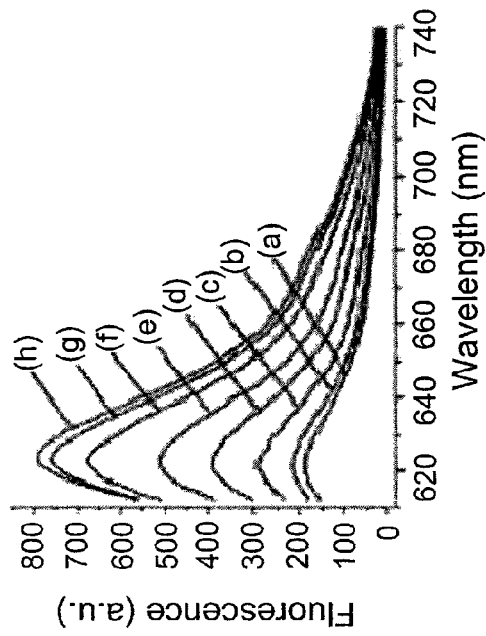
Fig. 3A Fig. 3B Fig. 3C Fig. 3D

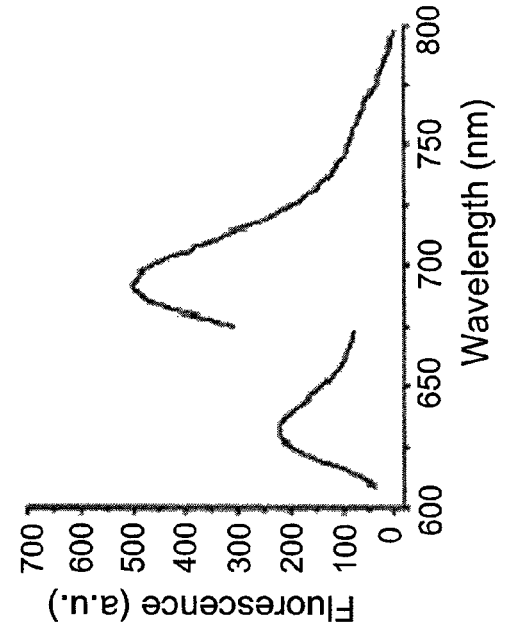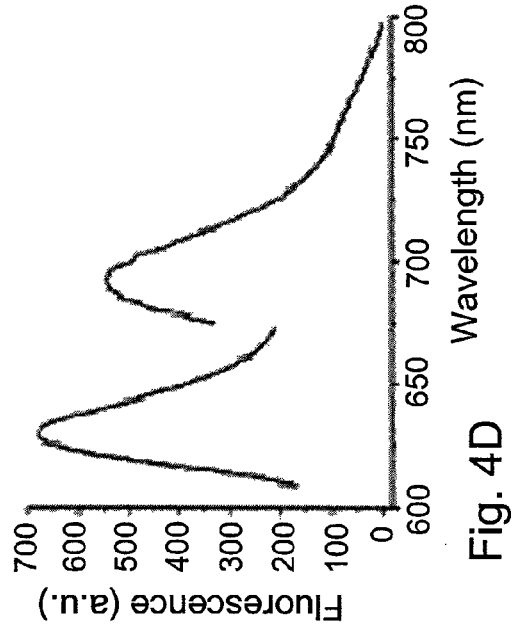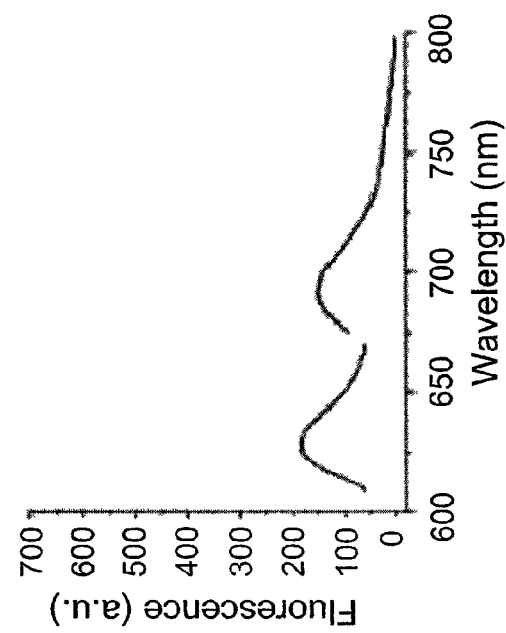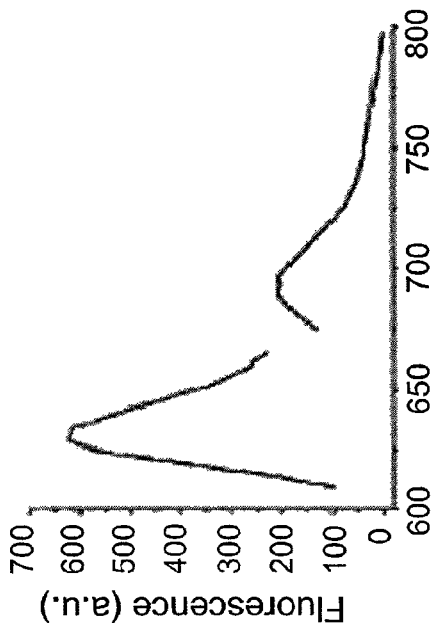

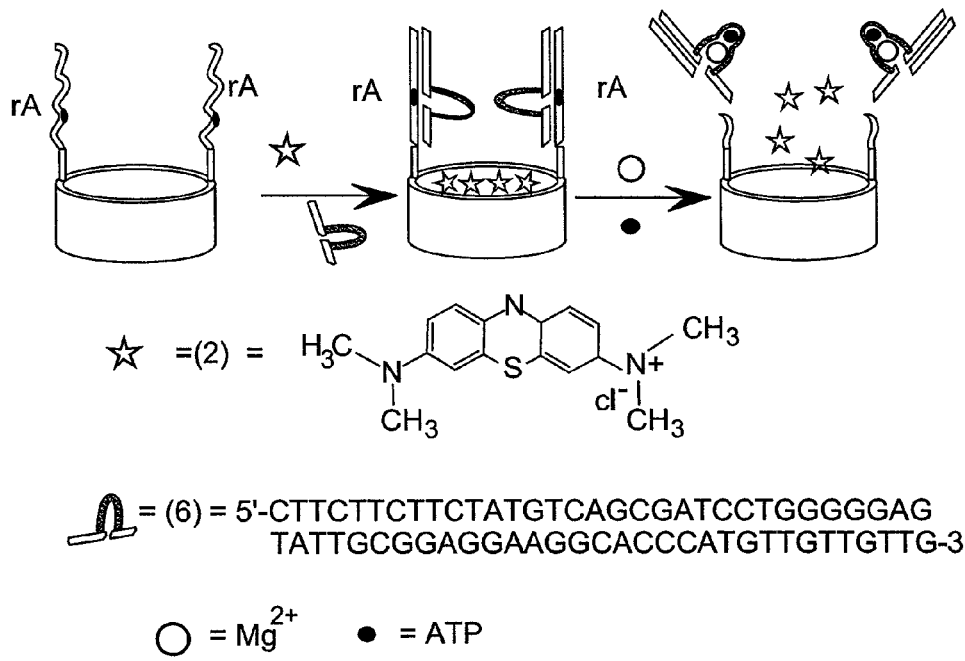
Fig. 5A
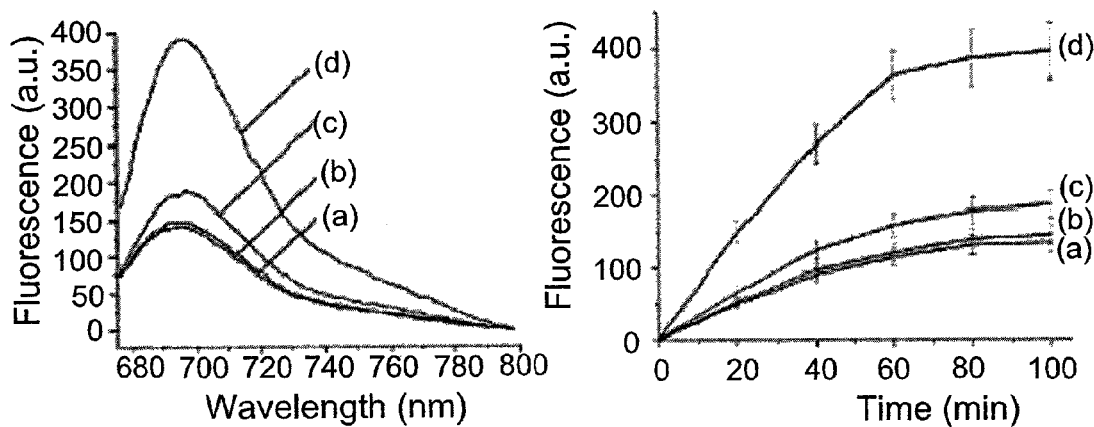
Fig. 5B
Fig. 5C

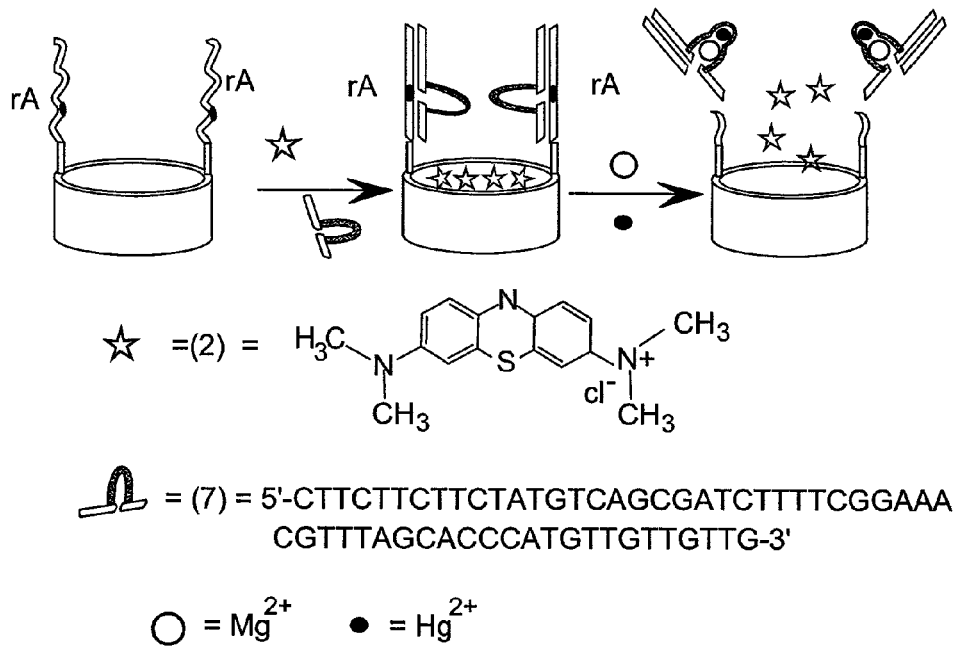
Fig. 6A
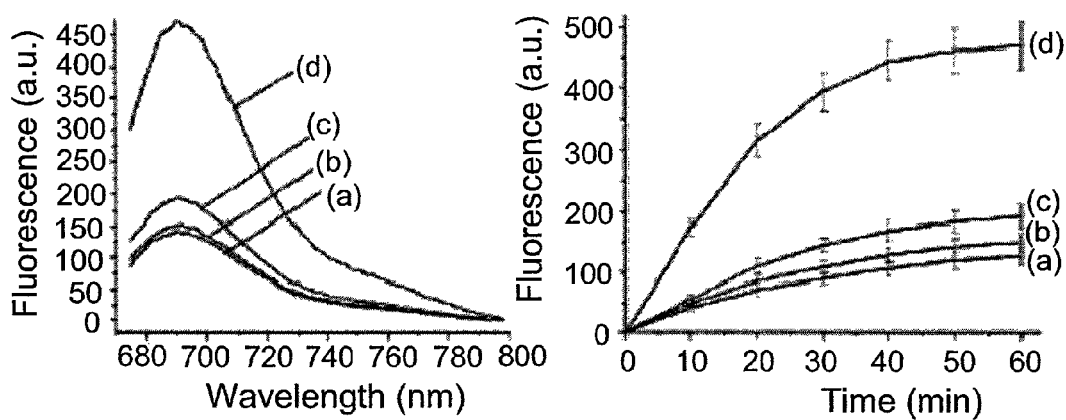
Fig. 6B
Fig. 6C

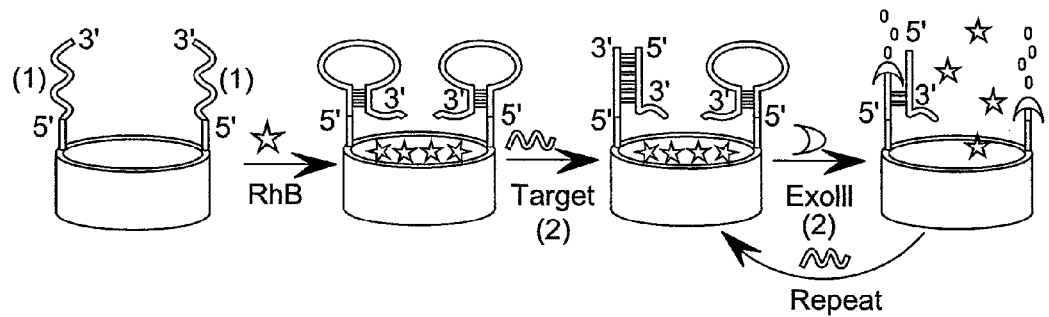
Fig.8A
Fig. 8B
Fig. 8C
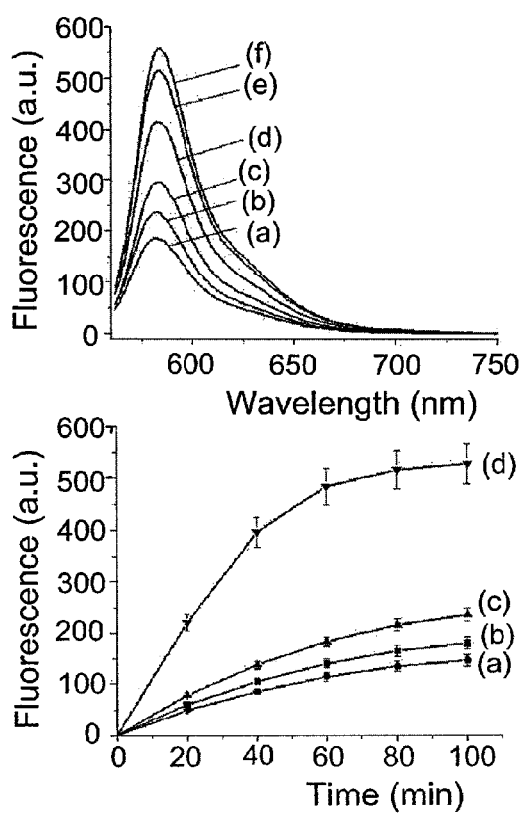
Fig. 8D
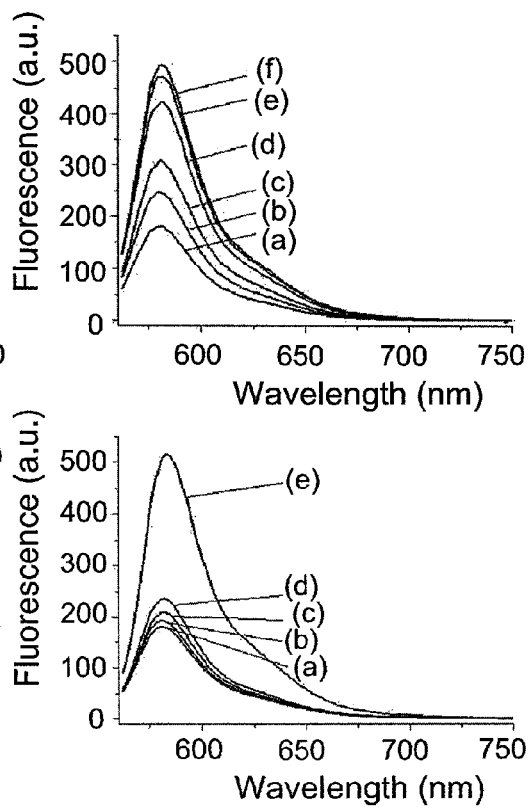
Fig. 8E

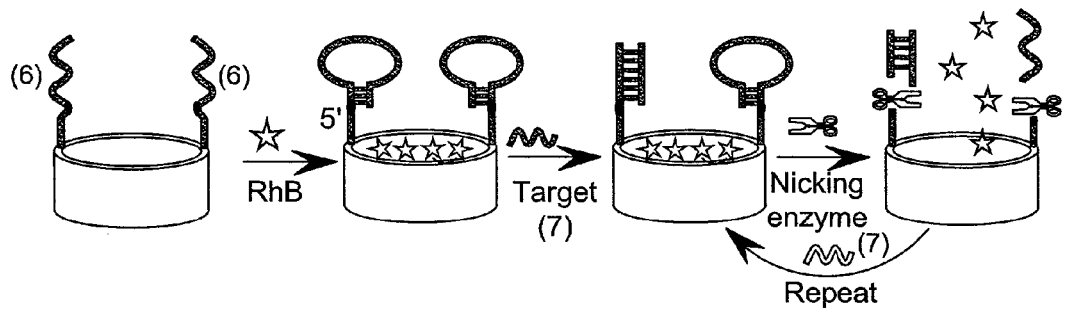
Fig. 9A
Fig. 9B
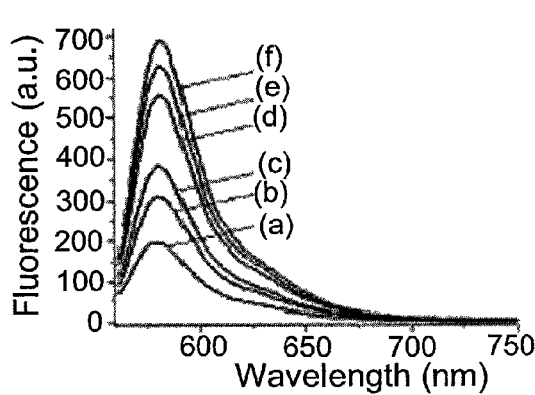
Fig. 9C
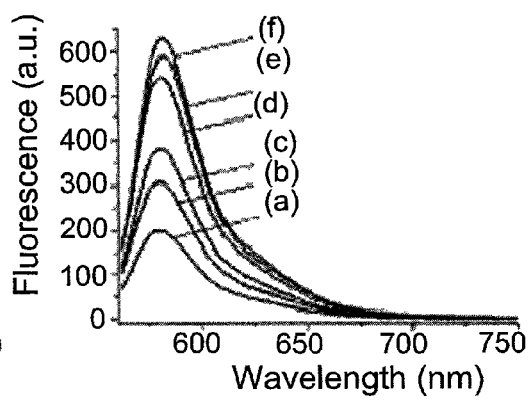
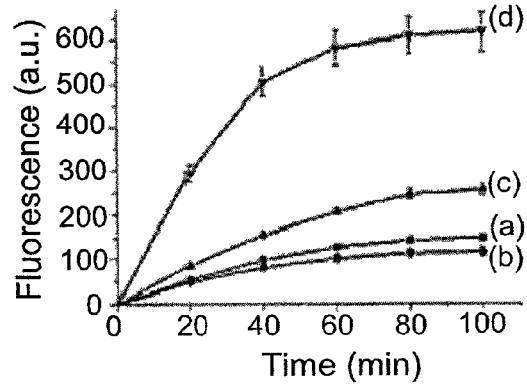
Fig. 9D
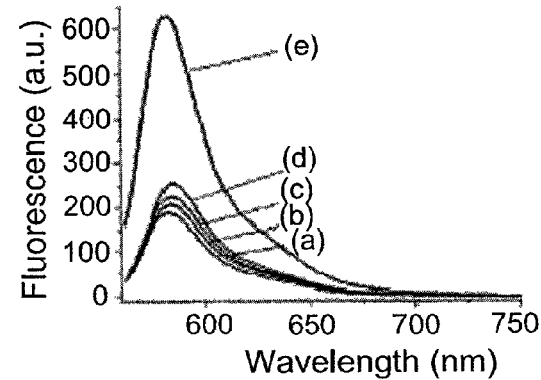
Fig. 9E

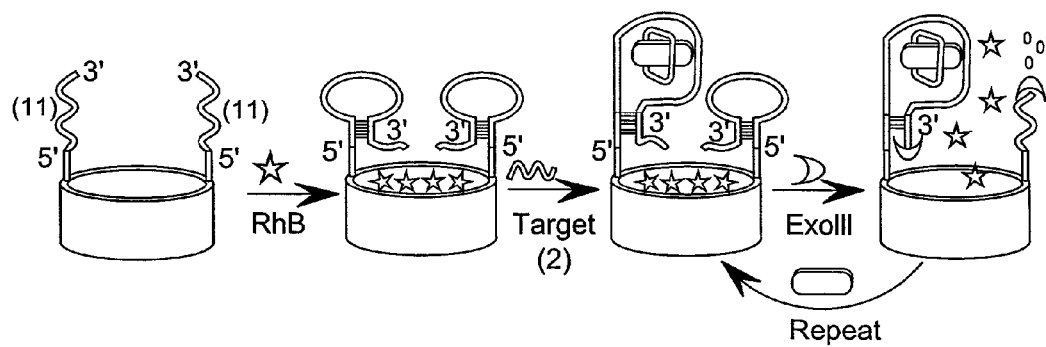
Fig.10A
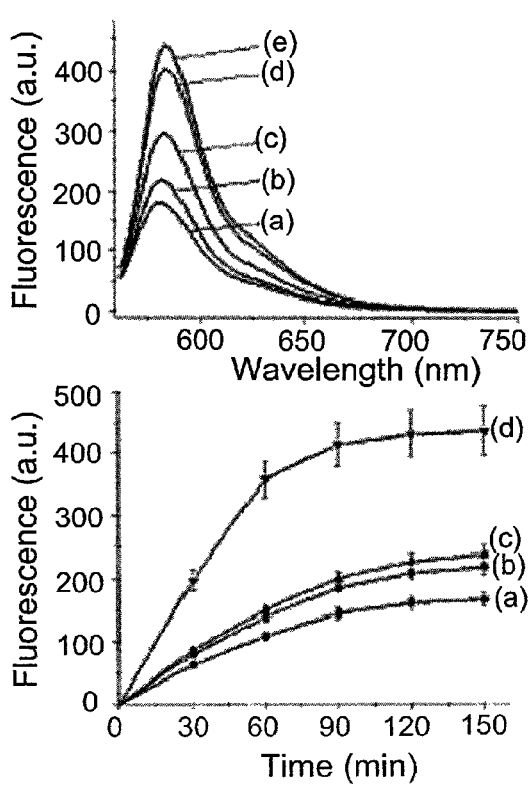
Fig. 10B
Fig. 10D
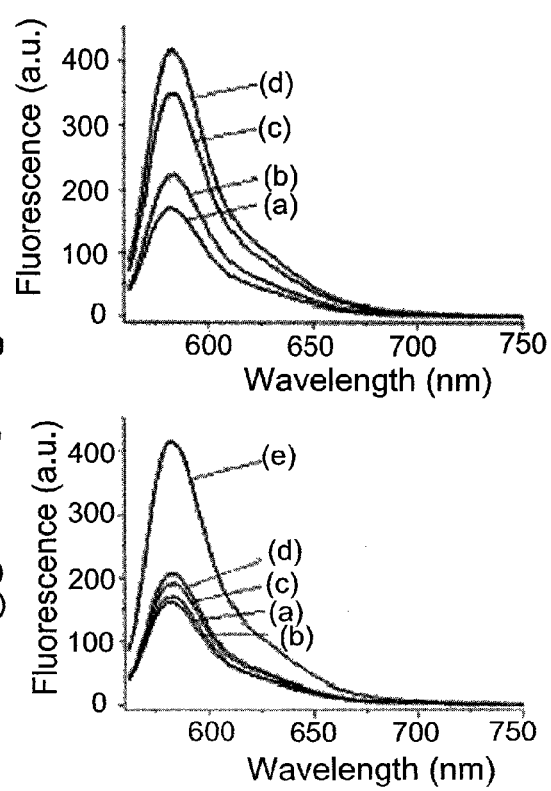
Fig. 10C
Fig. 10E

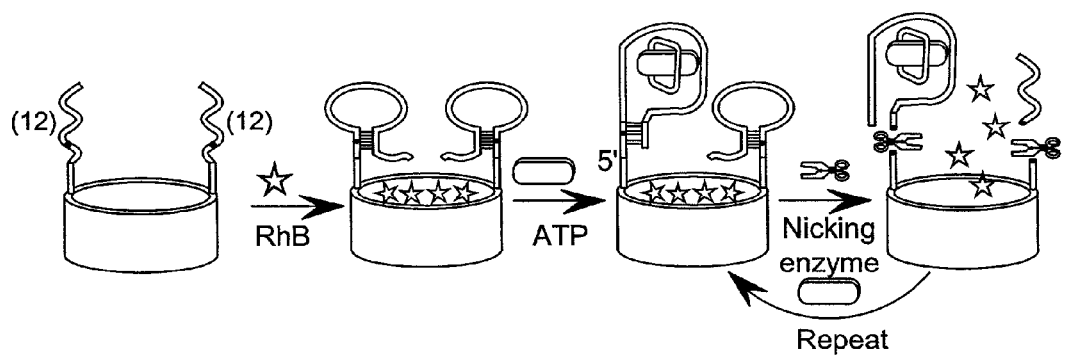
Fig. 11A
Fig. 11B
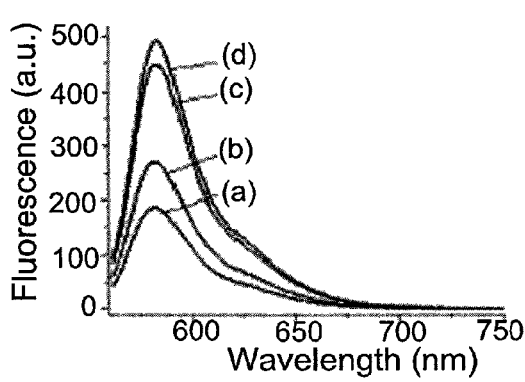
Fig. 11D
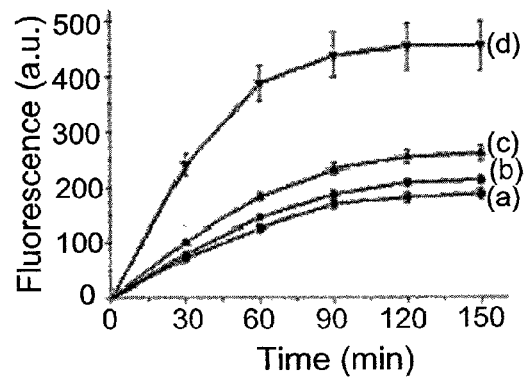
Fig. 11C
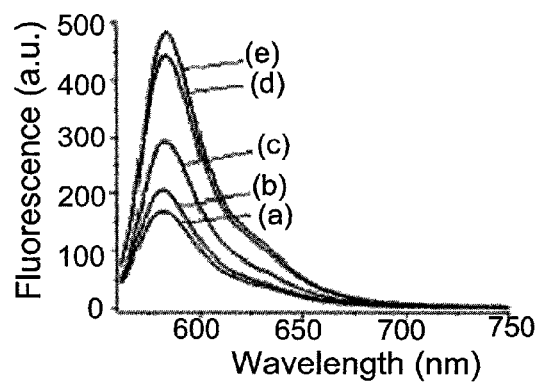
Fig. 11E
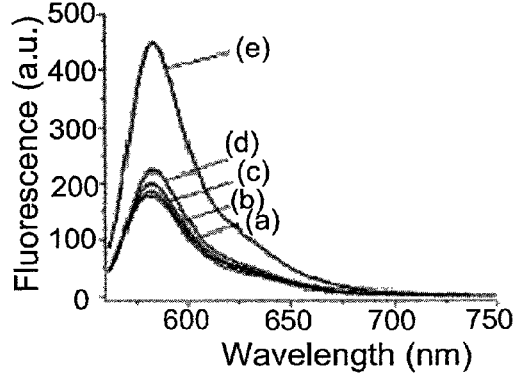

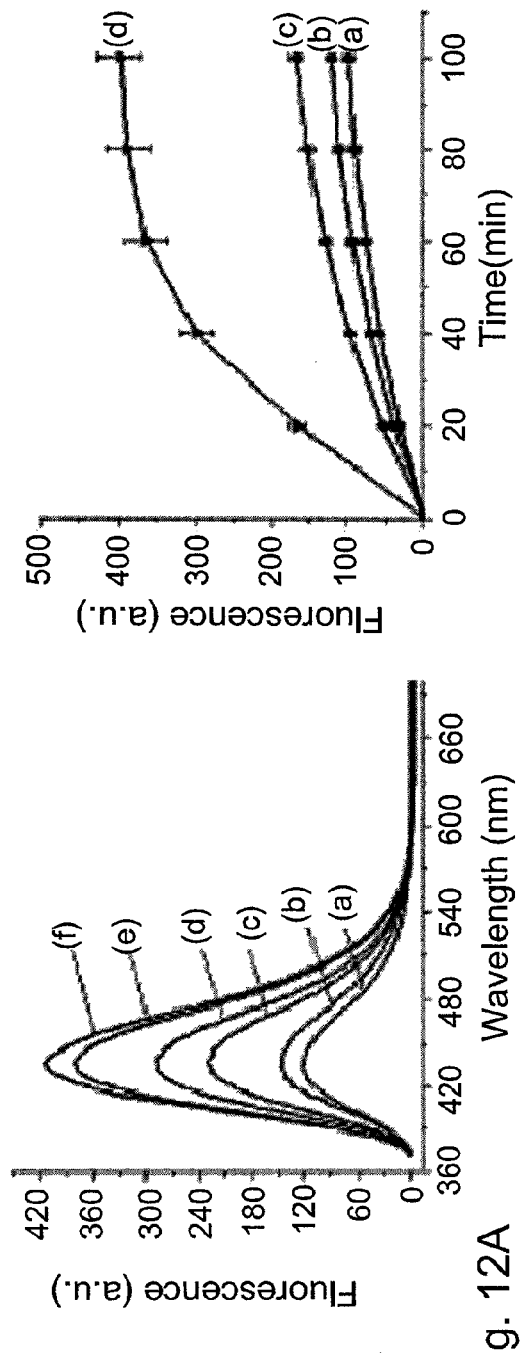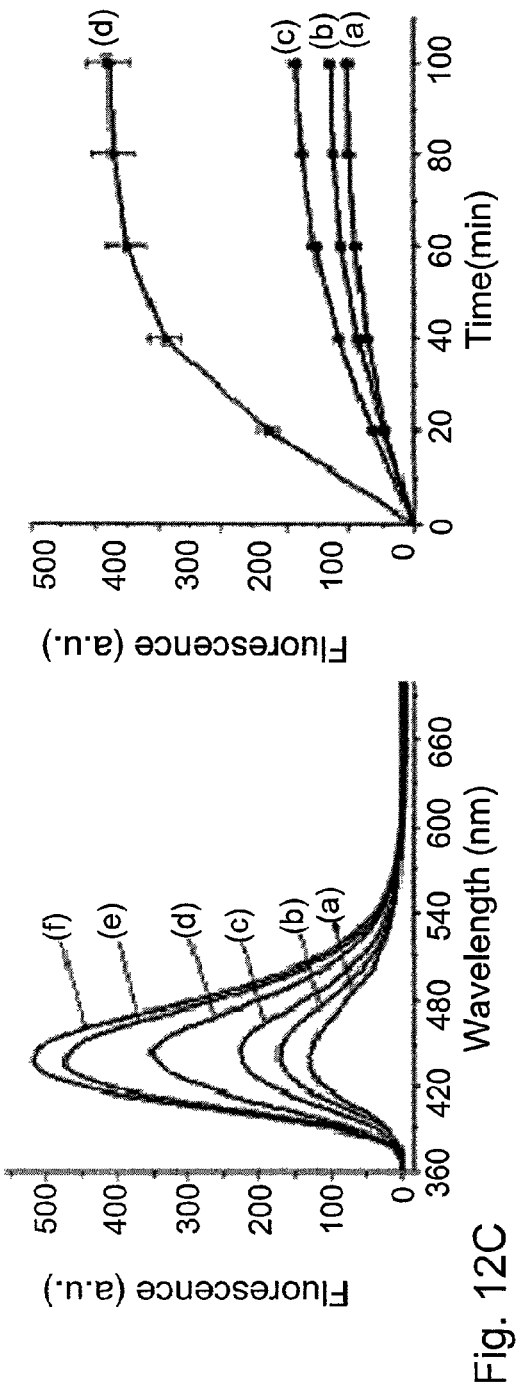
Fig. 12A  Fig. 12B  Fig. 12C  Fig. 12D

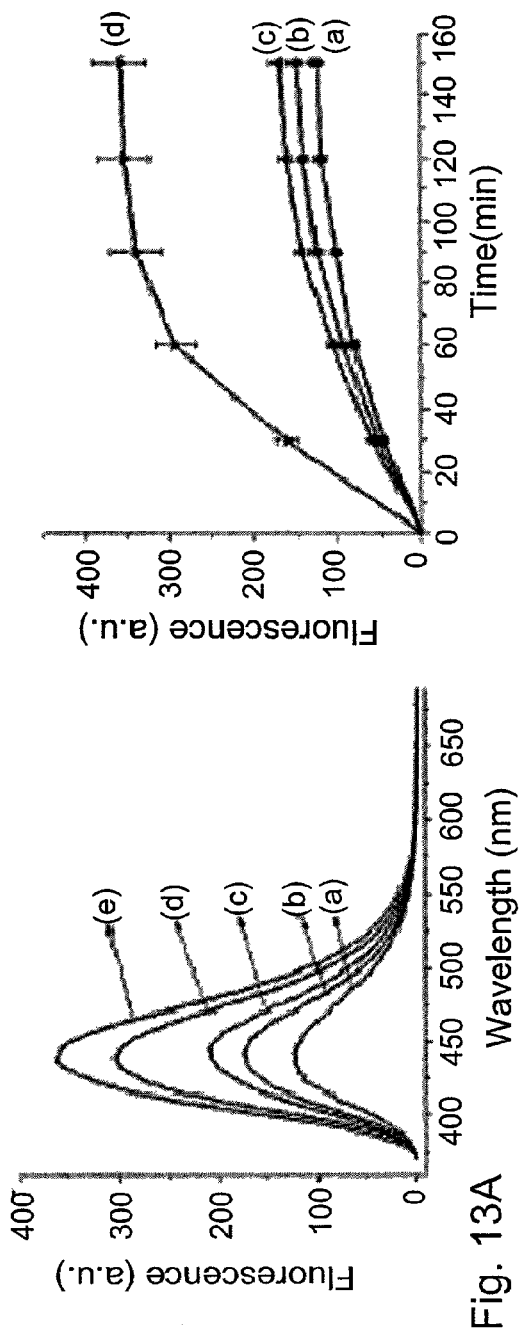
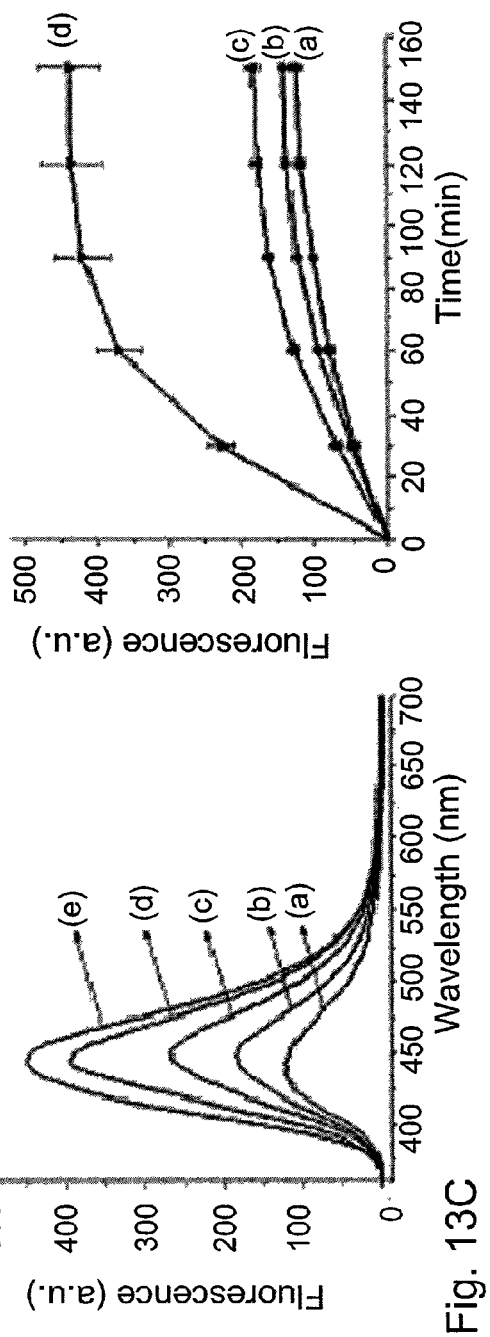
Fig. 13A
Fig. 13B
Fig. 13C
Fig. 13D

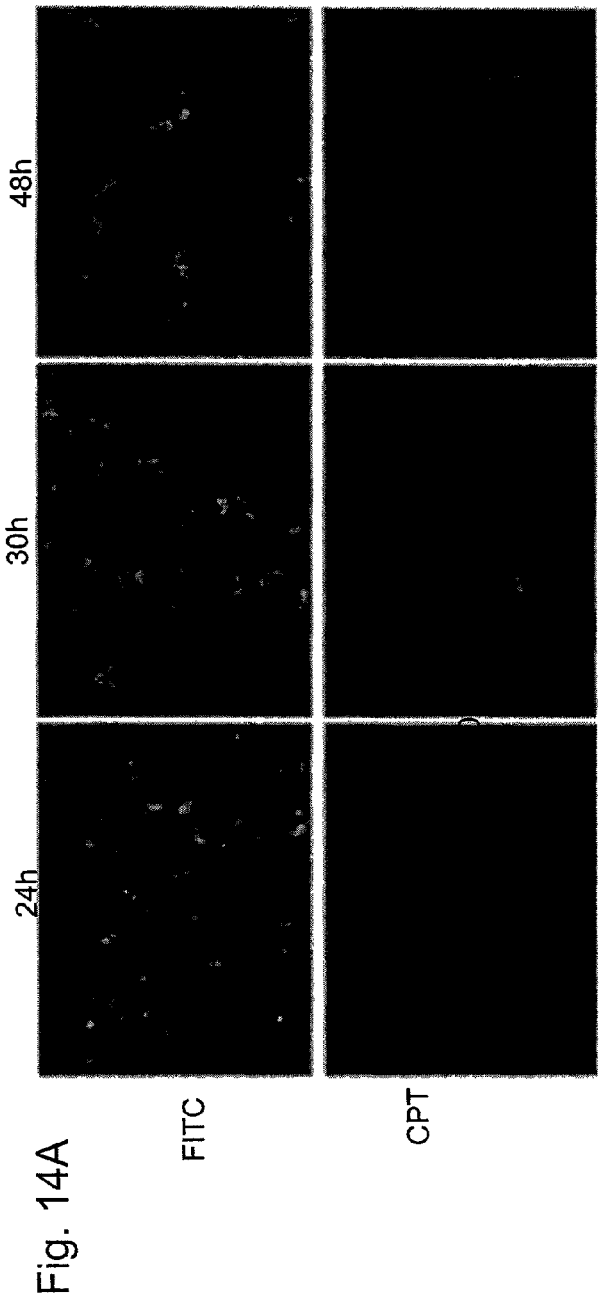
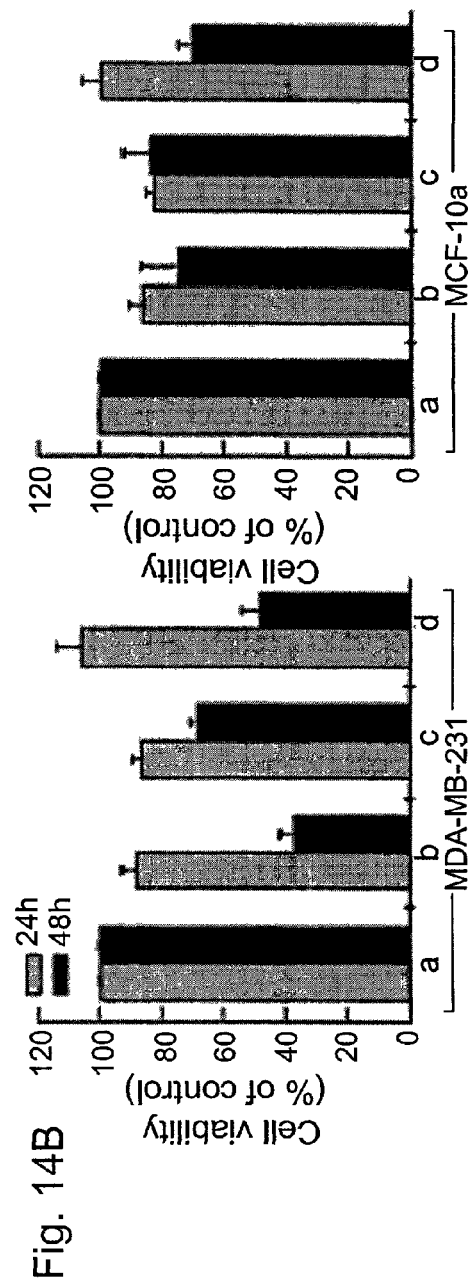
Fig. 14A
Fig. 14B

RECOGNITION-RELEASE NANOPOROUS SUBSTRATE COMPRISING ACTIVE AGENTS, METHODS OF THEIR PREPARATION AND USES

TECHNOLOGICAL FIELD

The invention relates of porous substrates embedding at least one active agent within pores capped with a nucleotidic sequence capable controlling the release of said agent upon associating with an analyte and forming a cleavage-prone conformation, including methods of their preparation and uses thereof in safe and effective administration of active agents and diagnosis.

PRIOR ART

References considered to be relevant as background to the presently disclosed subject matter are listed below:
1. Zhang et al. *ACS Nano*, 7(10), 8455-8468 (2013)
2. Zhang et al. *J. Am. Chem. Soc.* 135, 1934-1940 (2013)
3. Yang, Q.; Wang, S.; Fan, P.; Wang, L.; Di, Y.; Lin, K.; Xiao, F.-S. *Chem. Mater.* 2005, 17, 5999-6003.
4. Gao, Q.; Xu, Y.; Wu, D.; Shen, W.; Deng, F. *Langmuir* 2010, 26, 17133-17138.
5. Zheng, H.; Wang, Y.; Che, S. *J. Phys. Chem. C* 2011, 115, 16803-16813.
6. Liu, N.; Dunphy, D. R.; Atanassov, P.; Bunge, S. D.; Chen, Z.; Lopez, G. P.; Boyle, T. J.; Brinker, C. J. *Nano Lett.* 2004, 4, 551-554.
7. Aznar, E.; Casasus, R.; Garcia-Acosta, B.; Marcos, M. D.; Martinez-Manez, R.; Sancenon, F.; Soto, J.; Amoros, P. *Adv. Mater.* 2007, 19, 2228-2231.
8. Liu, R.; Zhao, X.; Wu, T.; Feng, P. *J. Am. Chem. Soc.* 2008, 130, 14418-14419.
9. Luo, Z.; Cai, K.; Hu, Y.; Zhao, L.; Liu, P.; Duan, L.; Yang, W. *Angew. Chem. Int. Ed.* 2011, 50, 640-643.
10. Wan, X.; Wang, D.; Liu, S. *Langmuir* 2010, 26, 15574-15579.
11. Yu, A.; Wang, Y.; Barlow, E.; Caruso, F. *Adv. Mater.* 2005, 17, 1737-1741.
12. Park, C.; Kim, H.; Kim, S.; Kim, C. *J. Am Chem. Soc.* 2009, 131, 16614-16615.
13. Lei, C.; Shin, Y.; Liu, J.; Ackerman, E. J. *J. Am. Chem. Soc.* 2002, 124, 11242-11243.
14. Takahashi, H.; Li, B.; Sasaki, T.; Miyazaki, C.; Kajino, T.; Inagaki, S. *Chem. Mater.* 2000, 12, 3301-3305.
15. Nguyen, T. D.; Tseng, H.-R.; Celestre, P. C.; Flood, A. H.; Liu, Y.; Stoddart, J. F.; Zink, J. I. *Proc. Natl. Acad. ScL USA* 2005, 102, 10029-10034.
16. Nguyen, T. D.; Liu, Y.; Saha, S.; Leung, K. C.-F.; Stoddart, J. F.; Zink, J. I. *J. Am. Chem. Soc.* 2007, 129, 626-634.
17. Li, D.; Wieckowska, A.; Willner, I. *Angew. Chem. Int. Ed.* 2008, 47, 3927-3931.
18. Miyake, Y.; Togashi, H.; Tashiro, M.; Yamaguchi, H.; Oda, S.; Kudo, M.; Tanaka, Y.; Kondo, Y.; Sawa, R.; Fujimoto, T.; Machina-mi, T.; Ono, A. *J. Am. Chem. Soc.* 2006, 128, 2172-2173.
19. Ono, A.; Togashi, H. *Angew. Chem. Int. Ed.* 2004, 43, 4300-4302.
20. Freeman, R.; Finder, T.; Willner, I. *Angew. Chem. Int. Ed.* 2009, 48, 7818-7821.
21. Huang, W. T.; Shi, Y.; Xie, W. Y.; Luo, H. Q.; Li, N. B. *Chem. Commun.* 2011, 47, 7800-7802.
22. Wang, Z.-G.; Elbaz, J.; Remade, F.; Levine, R. D.; Willner, I. *Proc. Natl.* Acad. Sci. USA 2010, 107, 21996-22001.
23. Liu, J.; Cao, Z.; Lu, Y. *Chem. Rev.* 2009, 109, 1948-1998.
24. Tombelli, S.; Minunni, M.; Mascini, M. *Biosens. Bioelectron.* 2005, 20, 2424-2434.
25. Willner, I.; Zayats, M. *Angew. Chem. Int. Ed.* 2007, 46, 6408-6418.
26. Li, D.; Shlyahovsky, B.; Elbaz, J.; Willner, I. *J. Am. Chem. Soc.* 2007, 129, 5804-5805.
27. Niazov, T.; Pavlov, V.; Xiao, Y.; Gill, R.; Willner, I. *Nano Lett.* 2004, 4, 1683-1687.
28. Liu, J.; Lu, Y. *J. Am. Chem. Soc.* 2004, 126, 12298-12305.
29. Liu, J.; Lu, Y. *J. Am. Chem. Soc.* 2007, 129, 9838-9839.
30. Dittmer, W. U.; Reuter, A.; Simmel, F. C. *Angew. Chem. Int. Ed.* 2004, 43, 3550-3553.
31. Shlyahovsky, B.; Li, D.; Weizmann, Y.; Nowarski, R.; Kotler, M.; Willner, I. *J. Am. Chem. Soc.* 2007, 129, 3814-3815.
32. Liu, Y.; Lin, C.; Li, H.; Yan, H. *Angew. Chem. Int. Ed.* 2005, 44, 4333-4338.
33. Kang, H.; O'Donoghue, M. B.; Liu, H.; Tan, W. *Chem. Commun.* 2010, 46, 249-251.
34. Liu, J.; Lee, J. H.; Lu, Y. *Anal. Chem.* 2007, 79, 4120-4125.
35. Seelig, G.; Soloveichik, D.; Zhang, D. Y.; Winfree, E. *Science* 2006, 314, 1585-1588.
36. Elbaz, J.; Lioubashevski, O.; Wang, F.; Remade, F.; Levine, R. D.; Willner, I. *Nature Nanotech.* 2010, 5, 417-422.
37. Winfree, E. Qian, L. *Science* 2011, 332, 1196-1201.
38. Chen, C.; Pu, F.; Huang, Z.; Liu, Z.; Ren, J.; Qu, X. *Nucleic Acids Res.* 2011, 39, 1638-1644.
39. He, D.; He, X.; Wang, K.; Cao, J.; Zhao, Y. *Adv. Funct. Mater.* 2012, DOI: 10.1002/adfm.201201343
40. Zhang, Y.; Yuan, Q.; Chen, T.; Zhang, X.; Chen, Y.; Tan, W. *Anal. Chem.* 2012, 84, 1956-1962.

Acknowledgement of the above references herein is not to be inferred as meaning that these are in any way relevant to the patentability of the presently disclosed subject matter.

BACKGROUND

Mesoporous silica (Si-MP) is a porous structure that allows the encapsulation of substrates in the pores, and its surface can be chemically modified. These properties were applied to use Si-MP as a versatile hybrid material for catalysis, drug delivery, and imaging. Furthermore, chemical modification of Si-MP enables the design of signal-responsive matrices for the controlled release of substrates from the pores of the matrices.

Different stimuli such as pH [2-5] photonic signals [6, 7], redox-reagents [8-10] or enzymes [11-14] were implemented to trigger the opening of the pores, leading to the controlled release of encapsulated substrates. Accordingly, the pores of the Si-MP were capped with gate units that lock the substrate in the pores, and allow the stimuli-responsive unlocking of the gates and the release of the substrates. For example, the photonic dethreading of semi-rotaxane pore-capping nanostructures were implemented to open the pores and release the stored substrate[15, 16].

The information encoded in the base sequences of nucleic acids provides a rich arena of opportunities to develop the area of DNA nanotechnology. Sequence-guided and pH-stimulated assembly of single-stranded DNA into i-motif structures or the cooperative binding of DNA duplexes by metal ions, e.g., by T-$Hg^{2+}$-T bridges were implemented to develop different DNA machines [17-19] and to develop logic gates [20, 21] and finite state logic machines [22]. Similarly, sequence-specific nucleic acid strands reveal specific binding properties toward low-molecular-weight or macromolecular substrates (aptamers) [23-25] or exhibit catalytic properties (DNAzymes) [26-29]. Aptamers have been implemented to develop DNA machines [30, 31] or to assemble programmed nanostructures, [32-34] and catalytic nucleic acids were used to develop logic gates, and logic gate cascades [35-37].

The conjugation of nucleic acids to mesoporous $SiO_2$ enabled the implementation of the signal-triggered functions of the DNA to "lock" and "unlock" the pores of the $SiO_2$. For example, the pores were loaded with a dye-substrate and "locked" by i-motif, C-quadruplex, capping units, and subsequently "unlocked" by separation of the bulky i-motif structure, to random single strand, at neutral pH values, thus allowing the release of the substrates [38]. In a related system the change of the pH and the opening of the pores was stimulated by a photochemical process.[39] Alternatively, the pores of the mesoporous $SiO_2$ were capped with duplex DNA units and the capping strands were separated by a strand displacement process, in the presence of $Hg^{2+}$ ions, to yield a T-$Hg^{2+}$-T bridged duplex structure of enhanced stability. The release of the pore-entrapped substrate, enabled the fluorescence detection of $Hg^{2+}$-ions [40].

It would be a major advance if one could design gated systems where the biocatalytic process is activated by a primary sensing or recognition event of an analyte or biomarker of particular interest, to ensure safe and efficient drug delivery to specific sites.

GENERAL DESCRIPTION

In its first aspect the invention provides a porous substrate comprising at least one active agent entrapped within said pores of said substrate; wherein said pores (i.e. the pore opening) are capped by at least one nucleic acid sequence having a locked conformation when said at least one active agent is entrapped within said pores; said capping nucleic acid sequence is capable of forming a cleavage-prone conformation upon association with at least one first analyte; thereby enabling said capping nucleic acid sequence to be cleaved and allowing the release of said embedded at least one active agent.

When referring to a porous substrate it should be understood to encompass any nanoporous material (being organic, metal, semi-metal or inorganic, either natural or artificial) framework supporting a regular, porous structure. The size of the pores is typically 100 nanometers or smaller. Said substrate can be in any form available, including nanoparticles, films, membranes and so forth. Non-limiting examples of porous substrate include activated carbon, zeolites, silica, zirconia, alumina and any combinations thereof. Said porous substrate can be a microporous material (having pore size of between about 0.2-2 nm), mesoporous material (having pore size of between about 2-50 nm) or macroporous material (having pore size of between about 50-1000 nm) or any combinations thereof.

The pores of said substrate entrap within them at least one active agent, thereby embedding said at least one active agent within said pore. In order to entrap and lock (i.e. maintain and keep) said at least one active agent within said pore, said pose opening (i.e. the part of said pore that is externally exposed to the surrounding environment) is capped by at least one nucleic acid sequence. Said capping is enabled by the chemical modification of the pore opening, i.e. chemically bonding said at least one nucleic acid sequence to said porous material at the pore opening.

The capping nucleic acid sequence (herein referred to also as the capping sequence or capping nucleic acid sequence) has a conformation (herein referred to as locked conformation) that enables the entrapment of said at least one active agent within said pores, thus allowing said at least one active agent to be kept within said pores without leaking to the surrounding environment of said substrate. Said capping nucleic acid sequence is a bio-resistant sequence comprises at least 5 nucleotides forming a macromolecule having a conformation that prior to association with at least one first analyte is able to cap the pore hole it is attached to and prevent said at least one active agent from diffusing out of the pore of said substrate and locking said active agent within the pore.

Upon association of said capping nucleic acid sequence with at least one first analyte said capping sequence is capable of forming a cleavage-prone conformation, i.e. a conformation different than the locked conformation wherein said capping sequence is available for cleaving (in some embodiments said change in conformation to the cleaved prone conformation allows the hydration of said sequence, the cleaving of said sequence by a biocatalyst and so forth). Only when the capping sequence forms said cleavage prone conformation is the session of the sequence possible (for example by means of exposing a nucleotide from its sequence to a biocatalyst). Cleavage of the capping sequence disconnects said sequence from the pore opening, by breaking at least one chemical bond in the capping sequence by said biocatalyst. Upon cleavage of capping sequence said at least one active agent entrapped within said pores of substrate is released to the immediate surrounding environment of said substrate.

In some embodiments said pores are capped by at least two independent nucleic acid sequences.

In other embodiments said capping nucleic acid sequence is either single or double stranded.

In some further embodiments said capping nucleic acid sequence comprises DNAzyme sequence. DNAzyme sequence (also known as deoxyribozymes, DNA enzymes or catalytic DNA) are DNA molecules that have the ability to perform a chemical reaction, such as catalytic action triggered by the association with a metal ion. Thus, in some embodiments, said cleavage of said capping sequence is enabled by said DNAzyme capping sequence itself. Thus, upon cleaving of said DNAzyme sequence a regeneration of target at least one first analyte is formed triggering the release of said active agent. Thus, the release of said agent from substrate is achieved by the presence of even small amounts of analyte (biomarker) making said substrate of the invention sensitive to a condition reflected in the presence of said biomarker.

In some further embodiments, said DNAzyme sequence is enlarged with foreign (additional) nucleotide domain (having at least 5 more nucleotides) having a free conformation (i.e. a conformation that does not include or associate with any compound) and an active conformation which is achieved upon associating of said foreign region with at least one second analyte (which can be the same or different than said first analyte); said foreign or additional nucleotide domain may be an aptamer binding sequence or an ion binding sequence, thus upon association of said additional domain with at least one aptamer or at least one ion said conformation of DNAzyme sequence is allosterically altered. Only upon reaching said active conformation the entire said DNAzyme sequence is capable of forming a cleavage-prone conformation upon association with said at least one first analyte thereby enabling cleavage of said capping nucleic acid sequence, and allowing the release of said embedded at least one active agent.

In other embodiments, said capping nucleic acid sequence comprises RNAzyme sequence.

In other embodiments said capping at least one nucleic acid sequence is a hairpin loop sequence. Said hairpin loop (or stem-loop intramolecular base pairing) is a pattern that can occur in single-stranded DNA or RNA sequences. Hairpin loop structure, or conformation occurs when two regions of the same strand, usually complementary in nucleotide sequence when read in opposite directions, base-pair to form a double helix that ends in an unpaired loop.

In some embodiments said at least two independent capping nucleic acid sequences are at least two independent hairpin loop sequences (which may be the same or different).

In some embodiments, said capping sequence with said at least one nucleic acid hairpin loop sequence forms a cleavage-prone conformation upon coupling association with at least one first analyte which is a nucleic acid strand, having complementary sequence thereby forming a double strand.

In some embodiments said capping sequence is selected from the following non-limiting list:

(1)
(SEQ. NO. 1)
5'-SH(CH2)6CAACAACATrAGGACATAGAAGAAGAAG-3'

(4)
(SEQ. NO. 2)
5'-CTTCTTCTTCTATGTCAGCGATCCGGAACGGCACCCATGTTGTTGT
T-G-3'

(5)
(SEQ. NO. 3)
5'-CTTCTTCTTCTATGTCTCCGAGCCGGTCGAAATGTTGTTG-3'

(6)
(SEQ. NO. 4)
5'-CTTCTTCTTCTATGTCAGCGATCCTGGGGGAGTATTGCGGAGGAAG-
GCACCCATGTTGTTGTTG-3'

(7)
(SEQ. NO. 5)
5'-CTTCTTCTTCTATGTCAGCGATCTTTTCGGAAACGTTTAGCACCCA
T-GTTGTTGTTG-3'

(8)
(SEQ. NO. 6)
5'-CTTCTTCTTCTATGTCTCATGGGGAGTATTGCGGAGGAAGGTCGA
AATGTTGTTG-3'

In other embodiments said capping sequence is selected from the following non-limiting list:

(1)
Tm = 67.3° C.
(SEQ. NO. 7)
5'-SH(CH2)6 CAA GGG CAG AAG TCT TCA CTG CCC TTG
CAC ACT-3'

(2)
(SEQ. NO. 8)
5'-AGT GTG CAA GGG CAG TGA AGA CTT GAT TGT-3'

(3)
(SEQ. NO. 9)
5'-AGT GTG CAA GAG CAG TGA AGA CTT GAT TGT-3'

(4)
(SEQ. NO. 10)
5'-AGT GTG CTA GAG CAG TGA AGA CTT GAT TGT-3'

(5)
(SEQ. NO. 11)
5'-AGT GTG CTA GAG CAG TTA AGA CTT GAT TGT-3'

(6)
Tm = 58.9° C.
(SEQ. NO. 12)
5'-SH(CH2)6AACGAAGCTGAGGATGTGTTCGTT-3'

(7)
(SEQ. NO. 13)
5'-ATCCTCAGCTTCG-3'

(8)
(SEQ. NO. 14)
5'-ATCCTGAGCTTCG-3'

(9)
(SEQ. NO. 15)
5'-ATCATGAGCTTCG-3'

(10)
(SEQ. NO. 16)
5'-ATCATGAGCGTCG-3'

(11)
Tm = 69.8° C.
(SEQ. NO. 17)
5'-SH(CH2)6CCTCCGCTACCTGGGGGAGTATTGCGGAGGAAGGTA-3'

(12)
Tm = 74.9° C.
(SEQ. NO. 18)
5'-SH(CH2)6CCTCCGCAATACTCCGCTGAGGCCTGGGGGAGTATTGCG
GAGGAAGGCCTCAGC-3'

At least one first analyte and/or at least second first analyte are each independently a biological substance being at least one nucleic acid strand, at least one peptide, at least one aptamer (DNA, RNA or peptide aptamer), at least one metal ion (such as for example $Mg^{+2}$, $Zn^{+2}$, $Hg^{+2}$), or any combinations thereof.

In some embodiments, said at least one first analyte and/or at least second first analyte is a biomarker for at least one ailment or condition. A biomarker, or biological marker, is any substance, compound or analyte that serves as an indicator of some biological state, condition or ailment. Biomarkers are measured and evaluated to examine normal biological processes, pathogenic processes, or pharmacologic responses to a therapeutic intervention. Thus, upon association of said capping sequence with said at least one first analyte and/or a least one second analyte a recognition of the condition associated with such analytes is performed by said substrate of the invention. Only upon such recognition event, does the capping sequence become prone to cleaving, thus releasing the active agent entrapped within the pores of said substrate only when needed. Thus, a substrate of the invention provides a safer administration method of an active agent (patient suffering lesser side effects since the agent is not released if no recognition is achieved) and more effective administration method since the release is performed at the site of analyte/biomarker presence.

In some embodiments said hairpin loop sequence comprises a nucleotide domain that enables the formation of said cleavage-prone conformation upon association with at least one analyte.

In some further embodiments, said hairpin loop sequence further comprises nucleotide domain having a free conformation and an active conformation upon associating with at least one second analyte.

In some embodiments said capping sequence comprises a nicking-enzyme specific nucleotide (i.e. a specific nucleotidic site that is prone to be nicked or cleaved by a nicking enzyme).

In some embodiments said cleavage is performed by a biocatalyst (i.e. an enzyme that catalyzes the cleavage or nicking of said capping sequence by catalytically reacting with said sequence so it is removed chemically from the pore opening). In some other embodiments said biocatalyst is an exonuclease or an endonuclease. In some further embodiments said biocatalyst is a nicking enzyme.

Exonucleases are enzymes that work by cleaving nucleotides one at a time from the end (exo) of a polynucleotide chain. A hydrolyzing reaction that breaks phosphodiester bonds at either the 3' or the 5' end occurs. Endonuclease, are enzymes that cleave phosphodiester bonds in the middle (endo) of a polynucleotide chain. A nicking enzyme (or nicking endonuclease) is an enzyme that cuts one strand of a double-stranded DNA at a specific recognition nucleotide sequences known as a restriction site. Such enzymes hydrolyse (cut) only one strand of the DNA duplex, to produce DNA molecules that are "nicked", rather than cleaved.

In some embodiments said substrate are semi-metal oxide nano-particles. In other embodiments said substrate is mesoporous silica nano-particles.

The term active agent should be understood to encompass any substance having a biological activity that is beneficial for the treatment and/or diagnosis of a patient administered therewith upon its release from the pores of said substrate. In some embodiments said at least one active agent is a pharmaceutical ingredient such as an anti-cancer drug, an anti-inflammatory drug, an anti-microbial drug, an anti-hypertensive drug, a neuroprotective agent, an anti-HIV agent and so forth and any combinations thereof. In other embodiments said active agent is a diagnostic agent capable of being detected upon its release from the pores of said substrate. Detection of said diagnostic agent can be performed by any method known in the art, such as for example magnetic resonance techniques, CT, PET, or any combinations thereof.

In a further aspect the invention provides a method of administering an active agent, which release is condition dependent, to a patient in need thereof, said method comprising administering to said patient a porous substrate comprising at least one active agent embedded within said pores of said substrate; wherein said pores are capped by at least one nucleic acid sequence having a locked conformation when said at least one active agent is entrapped within said pores; said capping nucleic acid sequence is capable of forming a cleavage-prone conformation upon association with at least one first biomarker associated with said condition; thereby enabling said capping nucleic acid sequence to be cleaved and allowing the release of said embedded at least one active agent.

The invention provides a porous substrate comprising at least one active agent embedded within said pores of said substrate; wherein said pores are capped by at least one nucleic acid sequence having a locked conformation when said at least one active agent is entrapped within said pores; said capping nucleic acid sequence is capable of forming a cleavage-prone conformation upon association with at least one first biomarker associated with at least one ailment, condition or disease or any symptoms thereof; thereby enabling said capping nucleic acid sequence to be cleaved and allowing the release of said embedded at least one active agent; for use in the treatment of said at least one ailment, condition or disease or any symptoms thereof.

The term treatment as used herein means the management and care of a patient for the purpose of combating a disease, aliment, disorder or condition or any symptoms thereof. The term is intended to include the delaying of the progression of the disease, aliment, disorder or condition or any symptoms thereof, the alleviation or relief of symptoms and complications, and/or the cure or elimination of the disease, aliment, disorder or condition or any symptoms thereof. The patient to be treated is preferably a mammal, in particular a human being.

The invention further envisages the aspect of a method of diagnosing a condition or ailment of a patient comprising administering to said patient a porous substrate comprising at least one agent embedded within said pores of said substrate; wherein said pores are capped by at least one nucleic acid sequence having a locked conformation wherein said at least one agent is entrapped within said pores; said capping nucleic acid sequence is capable of forming a cleavage-prone conformation upon association with at least one first biomarker of said condition or ailment; thereby enabling said capping nucleic acid sequence to be cleaved and allowing the release of said embedded at least one agent to the bodily fluid of said patient; and detecting said at least one agent in said bodily fluids of said patient.

The invention provides a method of preparing a porous substrate of the invention, said method comprising the steps of: (a) linking (i.e. forming a chemical bond at the pore opening) a porous substrate with at least one first single stranded nucleic acid sequence thereby forming a functionalized substrate; (b) contacting said functionalized porous substrate with at least one active agent thereby embedding said agent in the pores of said substrate; (c) contacting said embedded functionalized with a complementary second single stranded nucleic acid sequence thereby capping said pores (pore opening) of said porous substrate with said capping sequence and entrapping said at least one active agent in said pores; wherein said capping sequence is capable of forming a cleavage-prone conformation upon association with at least one first analyte.

In some embodiment of a method of the invention said second complementary single stranded nucleic acid sequence comprises a nucleotide domain having a free conformation and an active conformation upon associating with at least one second analyte; wherein active conformation of said second strand enables said capping sequence to form a cleavage-prone conformation upon association with at least one first analyte.

In a further aspect the invention provides a method of preparing a porous substrate of the invention, said method comprising the steps of: (a) linking a porous substrate with at least one hairpin single stranded nucleic acid sequence thereby forming a functionalized substrate; (b) contacting said functionalized porous substrate with at least one active agent at temperatures wherein said hairpin sequence is in a random conformation; thereby embedding said agent in the pores of said substrate; (c) lowering the temperature of said functionalized embedded substrate thereby forming said hairpin conformation and capping said pores of said porous substrate and entrapping said at least one active agent in said pores; wherein said capping sequence is capable of forming a cleavage-prone conformation upon association with at least one first analyte.

In some embodiments said at least one hairpin sequence comprises a nucleotide domain having a free conformation and an active conformation upon associating with at least one second analyte; wherein active conformation enables said capping sequence to form a cleavage-prone conformation upon association with at least one first analyte.

In a further embodiment of a method of the invention said capping sequence comprises a nicking enzyme specific nucleotide.

In a further aspect the invention provides a pharmaceutical composition comprising at least one porous substrate of the invention.

When referring to a pharmaceutical composition comprising at least one porous substrate of the invention it should be understood to encompass said at least one porous substrate of the invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association at least one porous substrate of the invention with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The pharmaceutical ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The inventors of the present application have introduced new concepts in the application of mesoporous SiO2 NPs as a nano-container for the controlling of the release of pore-entrapped substrates.

(i) Metal-dependent DNAzymes as functional components for "locking" and "unlocking" of the pores. The metal-ion-driven catalytic properties of the DNAzymes provided the trigger and the control of the release of the pore-entrapped substrates;

(ii) Implementation of a mixture of two mesoporous SiO2 matrices that were functionalized with $Mg^{2+}$- or $Zn^{2+}$-dependent DNAzymes, as catalytic triggers for the multiplexed opening of the respective pores. Furthermore, as different ion-dependent DNAzymes are operating at different pH values, one might program the DNAzyme-mediated opening of the pores by environmental pH changes. Such pH-changes can be modulated, also, by electrochemical or photochemical means (iii) The ion-driven opening of the pores and the release of two different fluorescent dyes was rationalized in terms of a logic operation where the ions act as inputs and the released fluorophores provide the readout output signals. Thus, the systems may be considered as "smart materials" for the input-guided release of substrates. Such a system may be used in controlled drug delivery, targeted release of drugs, and signal triggered promoter-producing activation of drugs.

(iv) The allosteric activation of the DNAzymes associated with the MP-SiO2 containers by aptamer substrate complexes and/or the toxic $Hg^{2+}$-ions. These systems are thus envisaged for use as autonomous sense-and-treat systems that provide a new facet to nano-medicine. The biomarker-guided formation of an aptamer complex or a toxic-metal-stimulated activation of a DNAzyme could provide instructive sensing (recognition) events into the autonomous release of counter-acting drugs.

The substrate of the invention provides a major advance since the designed gated systems where the biocatalytic process is activated by a primary sensing or recognition event of an analyte or biomarker of particular interest, and where the biocatalytic process recycles and regenerates the analyte. Such systems release a substrate (drug), as a result of detection of minute amounts of biomarkers.

The present invention has introduced a new capping and release mechanism of substrates entrapped in MP-SiO2 NPs. The mechanism is based on tailored nucleic acid caps that block the substrates in the pores of the NPs and the unlocking of the pores by analyte (biomarker)-induced rearrangements of the nucleic acid caps that undergo catalytic fragmentation in the presence of Exo III or a nicking enzyme. These coupled sensing/catalytic fragmentation processes lead to the regeneration of the analytes (biomarkers). The capping nucleic acid units recognize genes or molecular biomarkers through the formation of complementary duplex structures or aptamer-substrate complexes. The systems present sense-and-release nanostructures, and present means to amplify the sensing process that releases the entrapped substrate by the regeneration of the analyte (biomarker).

The biocatalytic process for releasing the substrate from the MP-SiO2 NPs was then applied to stimulate the release of the anti-cancer drug, camptothecin, CPT, from the respective locked pores using nucleic acid or ATP, as triggers for unlocking the pores in the presence of Exo III or the nicking enzyme, Nb. BbvCI. Since the metabolic synthesis of ATP is enhanced in cancer cells as compared to normal cells, and realizing that the biocatalyst EndoGI, exhibiting Exo III-type activities, is present in the cancer cells, the effects of the CPT-loaded MP-SiO2 NPs locked with the ATP-dependent hairpin (6) on the viability of MDA-231 breast cancer cells and MCF-10a normal breast cells was examined. It was demonstrated that after a time-interval of 48 hours a 65% cell death of the cancer cells was observed, where only 25% cell death was encountered with the normal cells. The higher CPT-induced death of the cancerous cells correlated well with the enhanced synthesis of ATP in the cancer cells. These results highlight the development of "smart" drug-loaded nanoporous nanoparticles that are unlocked and release the chemotherapeutic drug at target cancer cells by an intracellular biomarker (ATP).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-1B show the schematic presentation of an embodiment of the invention. FIG. 1A shows the SiO2 nanopores functionalized with the thiolated sequence (1), using the water soluble amine-sulfhydryl crosslinker N-ε-maleimidocaproyl-oxysulfosuccinimide ester (sulfo-EMCS). FIG. 1B shows the schematic presentation of the ion mediated release of MB+ or Th+ from the nano-containers, using the Mg2+-dependant or Zn2+-dependant DNAzyme, respectively.

FIGS. 2A-2D shows fluorescence spectra of MB+ in the solution upon addition of variable concentrations of Mg2+-ion to the dye-loaded SiO2 NPs: (a) 0 mM, (b) 0.1 mM, (c) 0.5 mM, (d) 1 mM, (e) 5 mM, (f) 10 mM, (g) 25 mM, (h) 50 mM; followed by the release of MB+ to the solution for a time interval of 60 minutes (FIG. 2A). FIG. 2B shows the calibration curve for the release of MB+ from the pores of the (1)/(4)-functionalized SiO2 NPs as a function of the Mg2+-ion concentration. FIG. 2C shows the time-dependant fluorescence changes upon the release of MB+. Curve (a)—upon the treatment of the (1)/(4)-functionalized SiO2 NPs with 10 mM Mg2+-ions; curve (b)—upon the treatment of the (1)/(4)-functionalized SiO2 NPs in the absence of Mg2+-ions. FIG. 2D shows the fluorescence changes of MB+ upon the treatment of the (1)/(4)-functionalized SiO2 NPs with different metal ions (10 mM) for a time interval of 60 minutes.

FIGS. 3A-3D show the fluorescence spectra of Th+ in the solution upon addition of variable concentrations of Zn2+-ion to the dye-loaded SiO2 NPs: (a) 0 mM, (b) 0.05 mM, (c) 0.1 mM, (d) 0.5 mM, (e) 1 mM, (f) 5 mM, (g) 10 mM, (h) 20 mM; followed by the release of Th+ to the solution for a time interval of 40 minutes. (B) Calibration curve for the release of Th+ from the pores of the (1)/(5)-functionalized SiO2 NPs as a function of the Zn2+-ion concentration. (C) Time-dependant fluorescence changes upon the release of Th+. Curve (a)—upon the treatment of the (1)/(5)-functionalized SiO2 NPs with 5 mM Zn2+-ions; curve (b)—upon the treatment of the (1)/(5)-functionalized SiO2 NPs in the absence of Zn2+-ions. (D) Fluorescence changes of Th+ upon the treatment of the (1)/(5)-functionalized SiO2 NPs with different metal ions (5 mM) for a time interval of 40 minutes. (The concentration of PDCA for the elimination of the Pb2+-interference was 10 mM).

FIGS. 4A-4D shows the dual fluorescence output of MB+ and Th+ (FIG. 4A) in the absence of any of the inputs, (0,0); FIG. 4B in the presence of Mg2+ (10 mM) and Zn2+ (0 mM), (1,0); FIG. 4C in the presence of Mg2+ (0 mM) and Zn2+ (5 mM), (0,1) and FIG. 4D in the presence of Mg2+ (10 mM) and Zn2+ (5 mM), (1,1).

FIG. 5A-5C relates to ion mediated release of MB+ from the nano-containers, using the Mg2+-dependant DNAzyme including the ATP aptamer sequence. FIG. 5A is a schematic presentation of the ion mediated release of MB+ from the nano-containers, using the Mg2+-dependant DNAzyme including the ATP aptamer sequence. FIG. 5B shows the fluorescence spectra of MB+ in the solution upon the addition of (a) 0 Mg2+, 0 ATP; (b) 0 Mg2+, 100 μM ATP; (c) 20 mM Mg2+, 0 ATP; (d) 20 mM Mg2+, 100 μM ATP, after a time interval of 90 minutes. FIG. 5C shows the time dependant fluorescence changes upon the re-lease of MB+ using 0 Mg2+, 0 ATP (curve (a)); 0 Mg2+, 100 μM ATP (curve (b)); 20 mM Mg2+(curve (c)), 0 ATP; 20 mM Mg2+, 100 μM ATP (curve (d)).

FIGS. 6A-6C relate to ion mediated release of MB+ from the nano-containers, using the Mg2+-dependant DNAzyme including a foreign sequence capable of forming a hairpin structure in the presence of Hg2+-ions. FIG. 6A is a schematic presentation of the ion mediated release of MB+ from the nano-containers, using the Mg2+-dependant DNAzyme including a foreign sequence capable of forming a hairpin structure in the presence of Hg2+-ions. FIG. 6B is the fluorescence spectra of MB+ in the solution upon the addition of (a) 0 Mg2+, 0 Hg2+; (b) 0 Mg2+, 1 μM Hg2+; (c) 20 mM Mg2+, 0 Hg2+; (d) 20 mM Mg2+, 1 μM Hg2+ after a time interval of 60 minutes. FIG. 6C is the time dependant fluorescence changes upon the release of MB+ using 0 Mg2+, 0 Hg2+(curve (a)); 0 Mg2+, 1 μM Hg2+(curve (b)); 20 mM Mg2+(curve (c)), 0 Hg2+; 20 mM Mg2+, 1 μM Hg2+(curve (d)).

FIG. 7B shows the fluorescence spectra of doxorubicin in the solution after a time interval of 90 minutes, using the (1)/(6)-modified MP-SiO2 NPs, in the presence of 0 Mg2+, 0 ATP (curve (a)); 0 Mg2+, 100 μM ATP (curve (b)); 20 mM Mg2+, 0 ATP (curve (c)); 20 mM Mg2+, 100 μM ATP (curve (d)).

FIGS. 8A-8E show the unlocking of hairpin-mesoporous SiO2 NPs and the release of rhodamine B, RhB, using an analyte-DNA biomarker as activator for opening the hairpins and implementing Exo III as biocatalyst for regeneration of the DNA-biomarker (FIG. 8A). FIG. 8B shows the fluorescence spectra corresponding to the release of RhB upon subjecting the MP-SiO2 NPs (10 mg) to different concentrations of the biomarker analyte in the presence of Exo III (1 U/μl), for a fixed time-interval of 60 min. (a) 0 nM; (b) 50 nM; (c) 100 nM; (d) 500 nM; (e) 1 μM; (f) 2.5 μM. FIG. 8C is the fluorescence spectra corresponding to the release of RhB upon subjecting the MP-SiO2 NPs (10 mg) to different concentrations of Exo III in the presence of a constant concentration of (2) (1 μM), for a fixed time-interval of 60 min. (a) 0 U/μl; (b) 0.05 U/μl; (c) 0.1 U/μl; (d) 0.5 U/μl; (e) 1 U/μl; (f) 2 U/μl. FIG. 8D is a time-dependent fluorescence changes observed upon the release of RhB from the MP-SiO2 NPs by: (a) the RhB-loaded system without treatment with the biomarker (2) or Exo III; (b) treatment of the RhB-loaded system only with the biomarker-DNA, (2), (1 μM) without adding Exo III; (c) treatment of the RhB-loaded system only with Exo III (1 U/μl) and without the addition of (2); (d) treatment of the RhB-loaded MP-SiO2 NPs with (2) (1 μM) and Exo III (1 U/μl). FIG. 8E is the fluorescence spectra of the release RhB upon treatment of the hairpin-locked, RhB-loaded MP-SiO2

Figure 1B:
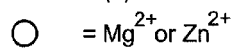

NPs with: (a) no DNA-biomarker; (b), (c) and (d) treatment with the one-, two-, three-base mutants DNA biomarker (3), (4) and (5), respectively, each 1 μM; (e) treatment with (2) (1 μM). In all experiments Exo III (1 U/μl) were included in the systems, and the fluorescence spectra were recorded after a fixed time-interval of 60 min.

FIGS. 9A-9E relates to the unlocking of hairpin-mesoporous SiO2 NPs and the release of rhodamine B, RhB, using an analyte-DNA biomarker as activator for opening the hairpins and implementing a Nb. BbvCI nicking enzyme as biocatalyst for regeneration of the DNA-biomarker (shown in FIG. 9A). FIG. 9B shows the fluorescence spectra corresponding to the release of RhB upon subjecting the MP-SiO2 NPs (10 mg) to different concentrations of the biomarker analyte in the presence of the Nb. BbvCI nicking enzyme (0.5 U/μl), for a fixed time-interval of 60 min. (a) 0 nM; (b) 50 nM; (c) 100 nM; (d) 500 nM; (e) 1 μM; (f) 2.5 μM. FIG. 9C shows the fluorescence spectra corresponding to the release of RhB upon subjecting the MP-SiO2 NPs (10 mg) to different concentrations of the Nb. BbvCI nicking enzyme in the presence of a constant concentration of (7) (1 μM), for a fixed time-interval of 60 min. (a) 0 U/μl; (b) 0.05 U/μl; (c) 0.1 U/μl; (d) 0.5 U/μl; (e) 1 U/μl; (f) 2 U/μl. FIG. 9D shows the time-dependent fluorescence changes observed upon the release of RhB from the MP-SiO2 NPs by: (a) the RhB-loaded system without treatment with the biomarker (7) or nicking enzyme; (b) treatment of the RhB-loaded system only with the biomarker-DNA, (7), (1 μM) without adding nicking enzyme; (c) treatment of the RhB-loaded system only with nicking enzyme (0.5 U/μl) and without the addition of (7); (d) treatment of the RhB-loaded MP-SiO2 NPs with (7) (1 μM) and nicking enzyme (0.5 U/μl). FIG. 9E shows the fluorescence spectra of the release RhB upon treatment of the hairpin-locked, RhB-loaded MP-SiO2 NPs with: (a) no DNA-biomarker; (b), (c) and (d) treatment with the one-, two-, three-base mutants DNA biomarker (8), (9) and (10), respectively, each 1 μM; (e) treatment with (7) (1 μM). In all experiments the Nb. BbvCI nicking enzyme (0.5 U/μl) was included in the systems, and the fluorescence spectra were recorded after a fixed time-interval of 60 min.

FIGS. 10A-10E relates to the unlocking of hairpin-gated MP-SiO2 NPs and the release of RhB by the opening of the hairpin gating units through the formation of ATP-aptamer complex, while regenerating the ATP-biomarker with Exo III (shown in FIG. 10A). FIG. 10B shows the fluorescence spectra corresponding to the release of RhB upon treatment of the hairpin-protected, RhB-loaded, MP-SiO2 NPs with variable concentrations of ATP in the presence of Exo III (1 U/μl), for a fixed time-interval of 90 min. (a) 0 μM; (b) 100 μM; (c) 500 μM; (d) 1 mM; (e) 2 mM. FIG. 10C shows the fluorescence spectra corresponding to the release of RhB from the RhB-loaded MP-SiO2 NPs upon treatment with variable concentrations of Exo III, and a constant concentrations of ATP (1 mM), for a fixed time-interval of 90 min. (a) 0 U/μl; (b) 0.1 U/μl; (c) 0.5 U/μl; (d) 1 U/μl. FIG. 10D shows the time-dependent fluorescence changes upon treatment of the RhB-loaded MP-SiO2 NPs: (a) with no ATP and no Exo III; (b) in the presence of only ATP (1 mM), without Exo III; (c) in presence of Exo III (1 U/μl) without ATP; (d) in the presence of ATP (1 mM) and Exo III (0.5 U/μl). FIG. 10E shows the selectivity studies demonstrating the specific unlocking of the pores by ATP. Fluorescence spectra corresponding to the release of RhB from the RhB-loaded MP-SiO2 NPs: (a) in the absence of ATP; (b), (c) and (d) in the presence of UTP, GTP, CTP, each 1 mM, respectively; (e) in the presence of ATP (1 mM). All fluorescence spectra were recorded in the presence of Exo III (1 U/μl), and after a fixed time-interval of 90 min.

FIGS. 11A-11E relates to the unlocking of hairpin-gated MP-SiO2 NPs and the release of RhB by the opening of the hairpin gating units through the formation of ATP-aptamer complex, while regenerating the ATP-biomarker with a Nb. BbvCI nicking enzyme (shown in FIG. 11A). FIG. 11B shows the fluorescence spectra corresponding to the release of RhB upon treatment of the hairpin-protected, RhB-loaded, MP-SiO2 NPs with variable concentrations of ATP in the presence of the Nb. BbvCI nicking enzyme (0.5 U/μl), for a fixed time-interval of 90 min. (a) 0 μM; (b) 100 μM; (c) 500 μM; (d) 1 mM; (e) 2 mM. FIG. 11C shows the fluorescence spectra corresponding to the release of RhB from the RhB-loaded MP-SiO2 NPs upon treatment with variable concentrations of the Nb. BbvCI nicking enzyme, and a constant concentrations of ATP (1 mM), for a fixed time-interval of 90 min. (a) 0 U/μl; (b) 0.1 U/μl; (c) 0.5 U/μl; (d) 1 U/μl. FIG. 11D shows the time-dependent fluorescence changes upon treatment of the RhB-loaded MP-SiO$_2$ NPs: (a) with no ATP and no nicking enzyme; (b) in the presence of only ATP (1 mM), without nicking enzyme; (c) in presence of nicking enzyme (0.5 U/μl) without ATP; (d) in the presence of ATP (1 mM) and nicking enzyme (0.5 U/μl). FIG. 11E shows the selectivity studies demonstrating the specific unlocking of the pores by ATP. Fluorescence spectra corresponding to the release of RhB from the RhB-loaded MP-SiO2 NPs: (a) in the absence of ATP; (b), (c) and (d) in the presence of CTP, UTP, GTP, each 1 mM, respectively. (e) in the presence of ATP (1 mM). All fluorescence spectra were recorded in the presence of the Nb. BbvCI nicking enzyme (0.5 U/μl), and after a fixed time-interval of 90 min.

FIGS. 12A-12D shows the fluorescence spectra corresponding to the release of CPT upon subjecting the MP-SiO2 NPs (10 mg) to different concentrations of the biomarker analyte in the presence of Exo III (1 U/μl), for a fixed time-interval of 60 min. FIG. 12A (a) 0 nM; (b) 50 nM; (c) 100 nM; (d) 500 nM; (e) 1 μM; (f) 2.5 μM. FIG. 12B shows the time-dependent fluorescence changes observed upon the release of CPT from the MP-SiO2 NPs by: (a) the CPT-loaded system without the biomarker (7) or Exo III; (b) treatment of the CPT-loaded system only with the biomarker (7) (1 μM), without Exo III; (c) treatment of the CPT-loaded system only with Exo III (1 U/μl) and without (7); (d) treatment of the CPT-loaded MP-SiO2 NPs with (7) (1 μM) and Exo III (1 U/μl). FIG. 12C shows the fluorescence spectra corresponding to the release of CPT upon subjecting the MP-SiO2 NPs (10 mg) to different concentrations of the biomarker analyte in the presence of the Nb. BbvCI nicking enzyme (0.5 U/μl), for a fixed time-interval of 60 min. (a) 0 nM; (b) 50 nM; (c) 100 nM; (d) 500 nM; (e) 1 μM; (f) 2.5 μM. FIG. 12D) Time-dependent fluorescence changes observed upon the release of CPT from the MP-SiO2 NPs by: (a) the CPT-loaded system without the biomarker (2) or nicking enzyme; (b) treatment of the CPT-loaded system only with the biomarker (2) (1 μM), without nicking enzyme; (c) treatment of the CPT-loaded system only with nicking enzyme (0.5 U/μl) and without the biomarker (2); (d) treatment of the CPT-loaded MP-SiO2 NPs with (2) (1 μM) and nicking enzyme (0.5 U/μl).

FIGS. 13A-13D shows the fluorescence spectra corresponding to the release of CPT upon treatment of MP-SiO2 NPs with variable concentrations of ATP, in the presence of Exo III (1 U/μl), for a fixed time-interval of 90 min. FIG. 13A (a) 0 μM; (b) 100 μM; (c) 500 μM; (d) 1 mM; (e) 2 mM. FIG. 13B) Time-dependent fluorescence changes upon treatment of the CPT-loaded MP-SiO2 NPs: (a) with no ATP and no Exo III; (b) in the presence of ATP (1 mM), without Exo III; (c) in presence of Exo III (1 U/µl), without ATP; (d) in the presence of ATP (1 mM) and Exo III (0.5 U/µl). FIG. 13C shows the fluorescence spectra corresponding to the release of CPT upon treatment of MP-SiO2 NPs with variable concentrations of ATP in the presence of the Nb. BbvCI nicking enzyme (0.5 U/µl), for a fixed time-interval of 90 min. (a) 0 µM; (b) 100 µM; (c) 500 µM; (d) 1 mM; (e) 2 mM. FIG. 13D shows the time-dependent fluorescence changes upon treatment of the CPT-loaded MP-SiO2 NPs: (a) with no ATP and no nicking enzyme; (b) in the presence of only ATP (1 mM) without nicking enzyme; (c) in presence of nicking enzyme (0.5 U/µl) without ATP; (d) in the presence of ATP (1 mM) and nicking enzyme (0.5 U/µl). 34 35

FIGS. 14A-14B show the cytotoxicity of CPT-MP-SiO2 in breast cancer cells (MDA-MB-231) compared to normal breast cells (MCF-10a). Cytotoxicity of CPT-MP-Si02 in breast cancer cells (MDA-MB-231) compared to normal breast cells (MCF-10a). FIG. 14A) Epi-fluorescence microscopy images of the MDA-MB-231 breast cancer cells with endoytored FITC-labeled and CPT-loaded MP-SiO2 NPs at different time intervals (Edocytosis was achieved by the treatment of the cell culture with 150 µg/ml of the silica NPs, see experimental section). Upper panel: green fluorescence of FITC, associated with the endocytosed particles. Lower panel: blue fluorescence of released CPT in the cells. FIG. 14B) Cell viability results at two time intervals (24 h, 48 h) corresponding to, panel I—MDA-MB-231 breast cancer cells; Pane II—normal MCF-10a breast epithelial cells: (a) Cells non-treated with the CPT-loaded MP-SiO2 NPs. (b) Cells treated with the CPT-loaded MP-SiO2 NPs. (c) Cells treated with free CPT, 20 µg/ml. (d) Cells pretreated with oligomycin, 25 µg/ml, and subsequently with the CPT-loaded MP-SiO2 NPs.

DETAILED DESCRIPTION OF EMBODIMENTS

In the present invention, metal-dependent catalytic nucleic acids were introduced as functional triggers for opening the pores of the mesoporous $SiO_2$ and the release of pore-entrapped fluorescence substrates. By the mixing of two kinds of mesoporous $SiO_2$ hybrids that are functionalized with the $Mg^{2+}$- or $Zn^{2+}$-dependent DNAzymes, as capping units that lock in the pores two different fluorophores, the selective (or multiplexed) release of a fluorophore is demonstrated by the respective substrates.

In addition, it was demonstrated that composite DNA structures consisting of the $Mg^{2+}$- or $Zn^{2+}$-sequences block the dye (entrapped substrates) in two kinds of pores of the mesoporous materials. The opening of the pores by the respective DNAzymes proceeds only upon the cooperative formation of aptamer-substrate complexes or metal-ion nucleic acid bridges, processes that trigger the formation of the active DNAzyme structures. Since the pores are opened in the presence of the specific ions ($Mg^{2+}$, $Zn^{2+}$) or upon the cooperative incorporation of aptamer substrate (ATP) or co-added metal ions ($Hg^{2+}$) these added components are considered as inputs for logic operations, the triggered opening of the pores, and the release of the entrapped substrates as outputs for these logic operations.

Mesoporous $SiO_2$ NPs (350-400 nm in diameter, were prepared according to Ref [51]. The pore diameter was estimated to be 3 nm and the surface area of the mesoporous composite corresponded to 632.8 $m^2/g$ and the average pore volume to $7.2 \times 10^{-2}$ $cm^3/g$. The NPs were functionalized with the thiolated ribonucleo-base containing sequence (1) according to FIG. 1A. (1) corresponds to the sequence of the substrate of $Mg^{2+}$-dependent-DNAzyme, the ($MP-SiO_2$-A) sequence and to the substrate of the $Zn^{2+}$-dependent DNAzyme ($MP-SiO_2$—B). The $MP-SiO_2$-A was interacted with methylene blue, MB+, (2), as guest substrate, whereas $MP-SiO_2$—B was subjected to a solution of thionine, $Th^+$, (3), to load the mesoporous nanoparticles, respectively. The MB+-loaded $MP-SiO_2$-A and the Th+-loaded $MP-SiO_2$—B were then treated with the respective $Mg^{2+}$ and $Zn^{2+}$-dependent DNAzyme sequences (4) and (5), respectively. The hybridization of the DNAzyme sequences (4) and (5) with the (1)-functionalized particles yield duplex structures that trapped the dyes MB+ or Th+ in the pores of $MP-SiO_2$-A or $MP-SiO_2$-B, respectively. The resulting $SiO_2$-NPs were extensively washed to remove any MB+ or Th+ units associated with surface domains outside the pores (see FIG. 2S). The resulting NPs retained dark colors of non-dissociable dyes, implying that the dyes are entrapped in the MP-SiO2 pores in locked configurations.

FIG. 1B depicts the principle of the ion-mediated, selective, release of the MB+ or Th+ dyes from the respective MP-SiO2 container matrices. In the presence of either Mg2+- or Zn2+-ions the active Mg2+- or Zn2+-dependent DNAzyme were generated on the (4)-MP-SiO2-A or (5)-MP-SiO2-B, respectively. This resulted in the cleavage of the substrates (4) and/or (5), respectively, leading to the dissociation of the duplex DNA plugs and the release of MB+ or Th+, respectively.

FIG. 2A, shows the fluorescence of MB+ observed in the bulk solution after a fixed time-interval of 60 minutes upon treatment of the (1)/(4) functionalized MP-SiO2-A with different concentrations of Mg2+. As the concentration of Mg2+ increases, the fluorescence of MB+, generated in the bulk, through the release from the pores, is intensified. FIG. 2B depicts the resulting calibration curve, indicating that at a Mg2+ concentration of ca. 10 mM the release of MB+ from the pores reaches a saturation value. FIG. 2C, curve (a), shows the time-dependent fluorescence changes upon treatment of the (1)/(4)-functionalized MP-SiO2-A with Mg2+-ions (10 mM). The fluorescence in the bulk solution increases with time and reaches a saturation value after ca. 60 minutes. For comparison, FIG. 2C, curve (b), depicts the time-dependent fluorescence changes in the solution upon treatment of the (1)/(4)-modified MP-SiO2-A in the absence of Mg2+. The fluorescence changes were substantially lower, and these may be attributed to desorption of residual MB+ from surface domain at the exterior of the pores, or to the slow leakage of MB+ from the incompletely blocked pores. From the fluorescence intensity obtained in the (1)/(4)-MP-SiO2-A system after 60 minutes of release of MB+, and using an appropriate calibration curve, we estimate that ca. 2.7 µmole/g SiO2 NPs of MB+ was released by the DNAzyme-mediated cleavage of the capping units. FIG. 2D shows the time-dependent fluorescence changes upon treatment the (1)/(4)-modified MP-SiO2-A NPs with different metal ions. Clearly, selectivity is demonstrated, and only in the presence of Mg2+, enhanced fluorescence in the bulk solution can be observed, as a result of the release of MB+ from the pores. These results indicate that the Mg2+-dependent DNAzyme cleaves off the duplex-DNA-locking units, thus enabling the release of MB+ from the pores. Particularly interesting, is the demonstrated selectivity, showing that the (1)/(4)-MP-SiO2-A composite is insensitive to Zn2+. This allows the selective activation of the (1)/(5)-MP-SiO2-B by Zn2+-ions and the release of thionine from this composite.

Similar results were demonstrated with the (1)/(5)-functionalized entrapped thionine, Th+, (3). FIG. 3A depicts the fluorescence intensities of Th+ in the bulk solution, upon treatment of the (1)/(5)-functionalized MP-SiO2-B NPs with different concentrations of $Zn^{2+}$-ions, for a fixed time-interval of 40 minutes. As the concentration of $Zn^{2+}$ increases the fluorescence in the bulk solution is intensified, consistent with the enhanced release of Th+ from the pores. The resulting calibration curve is shown in FIG. 3B, indicating that the fluorescence levels off to a saturation value at a $Zn^{2+}$ concentration of ca. 5 mM. FIG. 3C, curve (a) shows the time-dependent fluorescence changes upon treatment of the (1)/(5)-MP-SiO2-B in the presence of $Zn^{2+}$, 5 mM, while FIG. 4C, curve (b), depicts the time-dependent fluorescence changes in the absence of the $Zn^{2+}$ ions. Evidently, the time-dependent fluorescence changes are ca. 4.2-fold higher upon activation of the release of Th+ by the $Zn^{2+}$-dependent DNAzyme after a time interval of 40 minutes. From the fluorescence intensity obtained and using the appropriate calibration curve we estimate that ca. 3.9 µmole/g SiO2 NPs of Th+ was released from the pores. The time-dependent fluorescence changes in the absence of $Zn^{2+}$ ions are attributed to the leakage of Th+ from the pores due to incomplete blocking of the pores by the (1)/(5) duplexes and/or to residual Th+ desorbed from non-pore domain on the nanoparticles. The enhanced release of Th+ from the pores proceeds only in the presence of $Zn^{2+}$ ions, and all other added ions (except $Pb^{2+}$) do not affect the release of Th+ from the pores, FIG. 3D. The interference of $Pb^{2+}$ to the selective opening of the pores can be eliminated by the addition of 2,6-pyridine-dicarboxylic acid (PDCA), that act as a selective ligand for binding $Pb^{2+}$ ions.

In the presence of PDCA the $Pb^{2+}$-induced opening of the pores is eliminated, while the $Zn^{2+}$-ion-stimulated opening of the pores is unaffected. Thus, it is conclude that the $Zn^{2+}$-dependent DNAzyme activates only the release of Th+ from the (1)/(5)-MP-SiO2-B container. The treatment of the mixture consisting of the MB+-loaded (1)/(4)-MP-SiO2-A NPs, and of the Th+-loaded (1)/(5)-MP-SiO2-B NPs with $Mg^{2+}$- and $Zn^{2+}$-ions resulted in the release of MB+ and Th+ from the two kinds of nanoparticle containers. Accordingly, the $Mg^{2+}$ and $Zn^{2+}$ ions are considered as inputs for the activation of an "AND" logic gate operation, FIG. 4. A dual fluorescence output of MB+ and Th+ is considered as a "true" output, "1". Thus, in the absence of any of the inputs (0,0) only very low fluorescence is observed, output "0", FIG. 4A. In the presence of $Mg^{2+}$ or $Zn^{2+}$, inputs (1,0) or (0,1), only one intense fluorescence output of MB+ or Th+ is generated (out "0"), FIGS. 4(B) and (C). In the presence of $Mg^{2+}$- and $Zn^{2+}$-ions, intense fluorescence bands of the two dyes MB+ and Th+ were observed giving rise to an output "1", FIG. 4D, AND gate.

The activities of metal-dependent DNAzymes are controlled by conserved base sequences in the hairpin loops, that bind the respective metal ions, and by conserved sequences for the binding of the DNAzyme substrates. It was demonstrated that the incorporation of foreign bases into the sequence-specific loops of DNAzymes perturb the binding affinity of the loops towards the metal ions, presumably due to the flexibility of the added base chains, leading to a decrease in the DNAzyme activities. Thus, the incorporation of flexible foreign oligonucleotide sequences into the $Mg^{2+}$- or $Zn^{2+}$-sequence specific loops is anticipated to perturb the DNAzyme activities. The programming of these added foreign sequences, to bind auxiliary substrates/metal ions (e.g., by the formation of loops or duplexes) could however rigidify the loop sequence of the DNAzymes thus restoring the biocatalytic activities. That is, by the programming of aptamer sequences or inter-chain metal binding sequences into the DNAzyme loops, the allosteric activation of the DNAzymes through the formation of aptamer-substrate complexes or metal-ion-stabilized duplexes, are envisaged. This paradigm was implemented to affect the release of MB+ from the MB+-loaded MP-SiO2 through the ATP-aptamer complex aided or through the thymine-$Hg^{2+}$-thymine assisted activation of the $Mg^{2+}$-dependent DNAzyme. FIG. 5A shows schematically the nucleic acid nanostructure that leads to the ATP-guided assembly of the $Mg^{2+}$-dependent DNAzyme resulting in the release of MB+ from the pores. The nucleic acid (6) includes the base sequence characteristic to the $Mg^{2+}$-dependent DNAzyme and an inserted sequence comprising of the ATP aptamer sequence. The hybridization of (6) and the (1)-functionalized MS-SiO2 is anticipated to form a flexible loop structure revealing low affinity for binding of $Mg^{2+}$, thus, leading to an inefficient catalyst for cleaving (1), and releasing the pore-entrapped MB+. In the presence of ATP, the aptamer domain is expected to fold into a hairpin aptamer-ATP complex, thus leading to the rigidification of the DNAzyme sequence and to the spatial proximity of the bases associated with the DNAzyme sequence. Under these conditions, we expect that effective binding of $Mg^{2+}$ to the DNAzyme loop will proceed. This will activate the DNAzyme to cleave (1), while releasing MB+ from the pores.

Accordingly, MB+ was entrapped in the pores of the (1)-modified MP-SiO2 NPs through the hybridization of (6) to (1), using the (1)/(6) nanostructures as stopper units for the pores. FIG. 5B, curve (a), shows the fluorescence spectra of MB+ in the bulk solution upon stirring the (1)/(6)-MB+-locked MP-SiO2 NPs, for 90 minutes, in an aqueous solution. A low fluorescence band of MB+ is observed, that is attributed to the leakage of MB+ from the pores and the partial desorption of traces of MB+ associated with non-pore domains. FIG. 5B, curve (b), depicts the fluorescence intensity generated by the system in the presence of added ATP. No effect of ATP on the resulting fluorescence is observed, implying that ATP alone has no effect on the opening of the pores. In the presence of $Mg^{2+}$, but without added ATP, the fluorescence generated by the system increases by 40%, FIG. 5B, curve (c). This value of fluorescence should be compared to the fluorescence generated under similar conditions by the (1)/(4)-MP-SiO2 in the presence of $Mg^{2+}$ (3-fold fluorescence enhancement). Thus, the results indicate that the mutated strand (6), that includes the inserted aptamer sequence, exhibits low catalytic activity, presumably due to flexibility of the strand (5) that does not bind efficiently $Mg^{2+}$ ions. In turn, the addition of ATP to the system, and in the presence of $Mg^{2+}$ ions, results in the efficient release of the $MB^{2+}$ from the pores and a high fluorescence, FIG. 5B, curve (d). These results clearly imply that the formation of the ATP-aptamer complex results in the assembly of a rigidified loop for binding $Mg^{2+}$, leading to an effective catalyst for the cleavage of (1) and the opening of the pores. FIG. 5(C) shows the time-dependent fluorescence changes in the different systems. From the saturated fluorescence value generated by the ATP-aptamer-(1)/(6)-MB+-loaded MP-SiO2 system, and using an appropriate calibration curve, we estimated that after a time interval of 90 minutes ca. 1.9 µmole/g SiO2 NPs of MB+ were released from the pores. Very similar results are observed upon the insertion of the ATP aptamer sequence into the loop region of the $Zn^{2+}$-dependent DNAzyme, (see FIG. S3). We find that while the $Zn^{2+}$-DNAzyme mutated sequence is inefficient in releasing thionine from the MS-SiO2 pores, the allosteric formation of the ATP-aptamer complex assembles an active $Zn^{2+}$-DNAzyme loop that leads to the effective opening of the pores and the release of thionine.

The above demonstrates the allosteric activation of the $Mg^{2+}$-dependent DNAzyme and of the $Zn^{2+}$-dependent DNAzyme through the formation of aptamer-substrate complexes, thus leading to the triggered opening of the pores of the MP-SiO2 and to the effective release of MB+ or Th+ from the pores. Similar allosteric control of DNAzyme activity was achieved by using metal ions (e.g., $Hg^{2+}$) as promoters. This is exemplified in FIG. 6A, where the nucleic acid (7) includes two domains of the $Mg^{2+}$-dependent DNAzyme. A foreign sequence is inserted into the conserved DNAzyme sequence and it includes 6-thymine bases, capable of forming, in the presence of $Hg^{2+}$-ions, a T-$Hg^{2+}$-T bridged hairpin structure. Thus, the hybridization of (7) with the (1)-functionalized MP-SiO2 results in the locking of MB+ in the pores of the matrix. The enlarged loop structure of (7), and its flexibility, is anticipated to yield a poor nano-environment for the binding of $Mg^{2+}$, and thus an inefficient DNAzyme for "unlocking" the pores is formed. In the presence of $Hg^{2+}$-ions, the inserted sequence forms a hairpin T-$Hg^{2+}$-T bridged structure, and this contacts and rigidifies the DNAzyme loop structure. As a result, the added $Hg^{2+}$ allosterically activates the $Mg^{2+}$-DNAzyme structure, thus allowing the catalytic cleavage of (1), the opening of the pores and the release of the pore-loaded MB+. FIG. 6B depicts the fluorescence spectra of the bulk solution upon interacting the (1)/(7)-locked MB+-MP-SiO2 in the absence of $Mg^{2+}$ ions and $Hg^{2+}$ ions, curve (a), or only in the presence of $Hg^{2+}$ ions, curve (b). Only a residual low-intensity fluorescence is detected that is identical in the absence or presence of $Hg^{2+}$ ions. These results indicate that the $Hg^{2+}$ ions that interact with (7) do not promote the release of MB+ from the pores. Treatment of the (1)/(7)-MB+-loaded MS-SiO2 with $Mg^{2+}$-ions in the absence of $Hg^{2+}$, results in a very low increase in the fluorescence of the bulk solution, FIG. 6(B), curve (c), implying that the pores are still locked, resulting in the poor release of MB+. In the presence of co-added $Hg^{2+}$-ions and in the presence of $Mg^{2+}$-ions, a high fluorescence is generated in the bulk solution, indicating the effective release of MB+ from the pores (curve d). The time-dependent fluorescence changes upon releasing MB+ from the different systems are depicted in FIG. 6C. Thus, the co-added $Hg^{2+}$-ions act as an allosteric promoter for the $Mg^{2+}$-dependent DNAzyme that catalyzes the cleavage of (1) and the release of (2) from the system. From the saturation level of the fluorescence generated by the $Hg^{2+}$/$Mg^{2+}$-(1)/(7) MB+-loaded MP-SiO2, FIG. 6C, curve (d), and using the respective calibration curve we estimated that ca. 2.3 µmole/g SiO2 NPs of (2) were released from the pores after a time interval of ca. 60 minutes.

Figures 7A, 7B:
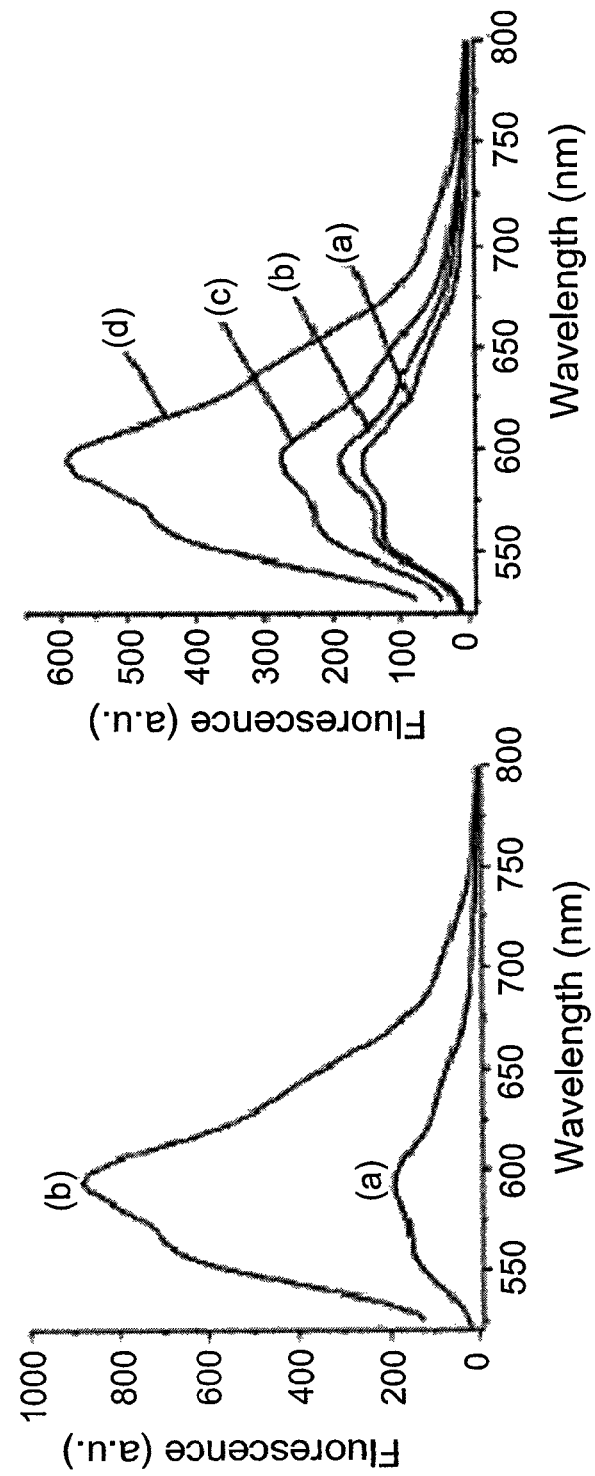
FIGS. 7A-7B show the fluorescence spectra of doxorubicin in the solution after a time interval of 60 minutes, using the (1)/(4)-modified MP-SiO2 NPs, in the absence (a) or in the presence (b) of 10 mM Mg2+-ion (FIG. 7A).

A model system of the $Mg^{2+}$-induced release of the anti-cancer drug doxorubicin was also examined FIG. 7A shows that the addition of $Mg^{2+}$-ions to the (1)/(4)-capped doxorubicin-entrapped SiO2 pores lead to the opening of the pores and the release of the drug. Particularly interesting is the ATP-cooperative synergetic $Mg^{2+}$-opening of the pores and the release of doxorubicin. The rapid metabolism observed in cancer cells generates extensive amounts of ATP, and thus the resulting ATP might act as an active unit for the targeted release of doxorubicin at cancer cells. FIG. 7B shows that the doxorubicin entrapped in the pores by their capping with (1)/(6) duplex structure is not released by ATP alone, inefficiently released by only $Mg^{2+}$-ions, yet efficiently released by the addition of ATP and $Mg^{2+}$-ions. That is, the binding of the ATP to the aptamer sequence of (6) rigidifies the loop sequence of the $Mg^{2+}$-dependant DNAzyme, thus leading to the effective cleavage of (1) and the opening of the pores.

The present invention further relates to DNA-gated mesoporous SiO2 nanoparticles, MP-SiO2 NPs, loaded with rhodamine B, RhB, act as "smart" materials that reveal complementary "sense" and "release" functionalities. The unlocking of the DNA pore-capping units is achieved by the biocatalytic cleavage of the DNA, and the unlocking process is amplified by the regeneration of the analyte-trigger. The RhB-loaded MP-SiO2 NPs are capped with nucleic acid hairpin structures that lock the RhB in the pores. Opening of the hairpin structures by a nucleic acid analyte trigger or by the formation of an aptamer-substrate (ATP) complex to the formation of duplex structures being cleaved by exonuclease III, Exo III, or the nicking enzyme, Nb. BbvCI. This results in the regeneration of the target analytes, the autonomous unlocking of the pores, and the release of RhB. The systems reveal selectivity and one-, two-, three-base mutations in the target DNA, or substitution of ATP with other nucleotide tri-phosphate, prohibit the unlocking of the pores. In analogy to the biocatalytic release of the model fluorophore substrates, the anti-cancer drug camptothecin, CPT, was entrapped in the pores, locked by the (1) or (11) hairpin structures. The drug was released from the pores in the presence of the nucleic acid (2) or ATP and the Exo III, as biocatalyst. Similarly, CPT locked in the pores by the (6) or (12) hairpins was released from the pores in the presence of ATP and Nb. BbvCI, as nicking enzyme, respectively. The effects of the CPT-loaded MP-SiO2 NPs, capped with the ATP dependent lock (6) on the viability of MDA-231 breast cancer cells and MCF-10a normal breast cells were examined. It was found that after 48 hours 65% cell death was observed for the MDA-231 cancer cells, where only 25% cell death was observed for the normal cells. The higher cell death of the cancer cells correlate well with the enhanced metabolic synthesis of ATP in the cancerous cells.

In addition, this invention envisages the gating of the pores of MP-SiO2 NPs with functional nucleic acids is described herein and the unlocking of the pores by a coupled recognition/biocatalytic effect. The recognition events of an analyte (biomarker) transform the capping element into a new functional element that undergoes biocatalytic scission. The scission process fragments a part of the capping unit and releases the analyte biomarker for the further autonomous catalytic degradation of the capping element, thus unlocking the pores and allowing the release of the pore-entrapped material. Thus, it is presented here, the assembly of "smart" model materials that sense biomarkers that trigger the autonomous biocatalytic unlocking of the pores and the release of substrates (analogs for drugs) from the pore containers. The biocatalytic regeneration of the biomarkers provides an amplification mechanism where a low amount of biomarkers allows the release of high content of entrapped substrate (drug).

Aminopropylsiloxane-MP-SiO2 NPs (300~400 nm in diameter) were prepared according to the reported method in Chen, C.; Pu, F.; Huang, Z.; Liu, Z.; Ren, J.; Qu, X. *Nucleic Acids Res.* 2011, 39, 1638-1644. The mesoporous materials exhibited a surface area corresponding to 733 m2/g, an average pore diameter of 2-3 nm and average pore volume of 0.19 cm3/g.

FIG. 8(A) depicts one coupled sensing/biocatalytic unlocking process that implements nucleic acid functionalized MP-SiO2 NPs and exonuclease III, Exo III, 36-38 as biomarker regeneration biocatalyst. Exo III requires for its biocatalytic activity a duplex structure, and it hydrolytically digests the 3'-end of the duplex DNA structure. Accordingly, the 5'-end of the nucleic acid (1) was covalently-linked to amine-functionalized MP-SiO2 NPs using sulfo-EMCS as covalent cross-linker. The nucleic acid (1) includes a tailored base sequence that generates at room temperature a hairpin structure that includes a single-stranded loop for the recognition of a nucleic acid biomarker. The hairpin structure reveals, however, a low melting temperature (67.3° C.), and, thus, exists at higher temperatures in a random coil single-stranded configuration, and at room temperature (25° C.) it folds to the energetically-stabilized hairpin structure. Thus, the pores of the MP-SiO2 are loaded with rhodamine B, RhB, as fluorescent dye, at 90° C., where the nucleic acid (1) is in the random coil configuration. The system was then allowed to cool to 25° C., where (1) folds into the hairpin structure. The MP-SiO2 NPs loaded with RhB are colored with the dye, but the fluorescent dye is non-removable, implying that the dye is, indeed, trapped in the pores. Following the washing of the MP-SiO2 NPs for the removal of any fluorescent dye linked to the exterior region outside the pores. Treatment of the (1)-capped MP-SiO2 NPs with the analyte (biomarker) nucleic acid (2) results in the opening of the hairpin to form a duplex structure. The 3'-end of the duplex structure is hydrolytically "digested" by Exo III, resulting in the shortage of (1) and the release of the analyte (biomarker) strand (2). The later strand opens a further hairpin structure and leads to the subsequent cleavage of the resulting duplex through the digestion of the 3'-end. That is, the analyte (biomarker) is sensed by the hairpin structure and it triggers-on the autonomous Exo III regeneration of the analyte and the unlocking of the pores, while releasing RhB. Note that the analyte (biomarker) strand, (2), is not affected by Exo III, since it includes a single stranded 3'-ended nucleic acid tether. FIG. 8(B) shows the fluorescence intensities of the released RhB, after a fixed time-interval of 60 minutes, and in the presence of 1 U/µl Exo III, using different concentrations of the analyte-biomarker to trigger the opening of the pores. As the concentration of the analyte-biomarker increases, the content of the released dye within the time-interval of 60 minutes is higher, consistent with the increase in primary opening of the hairpins by (2) that triggers the regeneration of the target-biomarker and the Exo III-stimulated opening of the pores. Similarly, FIG. 8(C) shows the fluorescence intensities of the released RhB in the presence of the (1)-capped MP-SiO2 NPs, and a fixed concentration of the analyte-biomarker (2), 1 µM, upon treatment with different concentrations of Exo III for a fixed time-interval of 60 minutes. Evidently, as the concentration of Exo III increases, the amount of the released RhB is higher, consistent with the enhanced opening of the hairpin-locked MP-SiO2 NPs by the autonomous Exo III regeneration of the target biomarker units. FIG. 8(D) shows the rate of 7 release of RhB from several control systems that include the RhB-entrapped MP-SiO2 NPs. The entrapped RhB leaches out from the hairpin-capped pores even in the absence of the target analyte-biomarker, curve (a). The leakage of RhB is very similar in the presence of only the target or the Exo III, curves (b) and (c), respectively. The rapid release of RhB proceeds only in the presence of the analyte target (1 µM) and Exo III (1 U/µl), curve (d). After 60 minutes the released RhB reaches a saturation value. Using an appropriate calibration curve, it was estimated that the release amount of RhB is ca. 8.5 µmol/g MP-SiO2 NPs. The release process of RhB from the MP-SiO2 NPs is, also, very sensitive to the primary sensing of the biomarker-analyte. FIG. 8(E) shows that one-, two- or three-base mutations in the target-biomarker, strands (3), (4), and (5), respectively, do not open the hairpin-capping units and do not activate the Exo III autonomous cleavage of the capping units. The release of the RhB using (3), (4) or (5) as analyte-biomarkers, and in the presence of Exo III, proceeds inefficiently and is very similar to the background leakage of RhB from the channels, FIG. 8(D), curves (a), (b) and (c).

A further biocatalytic-stimulated opening of hairpin-nucleic acid capped pores of MP-SiO2, and the release of the entrapped substrate is described in FIG. 9(A). The MP-SiO2 NPs are functionalized with the nucleic acid (6) by binding the 5'-end of the nucleic acid covalently to the amine-functionalized MP-SiO2 NPs, using sulfo-EMCS as cross-linker. At 90° C. (6) exists as a single-stranded chain, while at 25° C. the chain stabilizes into a hairpin structure. Thus, the pores of the MP-SiO2 NPs are loaded with RhB at 90° C. and the cooling of the system results in the hairpin-locked RhB in the pores. The interaction of the hairpin-capped pores with the analyte-biomarker (7) results in the formation of the duplex structure (6)/(7), that still acts as a structural stopper of the pores. Nonetheless, the duplex structure (6)/(7) is tailored in such a way that it includes the programmed duplex sequence for the specific nicking of one base in the duplex (marked with a spot). Nicking of strand (6) leads to a separation of an unstable duplex structure that yields the waste strand (7) and regenerates the analyte-biomarker for a secondary opening of a hairpin and nicking of the resulting duplex stopper. Note that the hairpin, generated by the folding of (6), does not include the appropriate duplex domain for being nicked, and this domain is formed only upon the hybridization of the analyte-biomarker with the single-stranded sensing loop of the hairpin. Thus, the hybridization of the analyte-biomarker with the hairpin capping units, triggers-on the nicking of the pore-gating units and the regeneration of the analyte-biomarker for the autonomous release of the capping units and the subsequent release of the entrapped substrate (RhB). The rate of release of RhB is controlled by the concentration of the analyte-biomarker (7) that opens the locking hairpin capping units. FIG. 9(B) depicts the fluorescence intensities of the released RhB upon treatment of the (6)-capped MP-SiO2 NPs with variable concentrations of the analyte-biomarker, for a fixed time interval of 60 minutes and a constant amount of the Nb.BbvCI nicking enzyme corresponding to 0.5 U/µl. As the concentration of the analyte-biomarker increases, the fluorescence of the released RhB is intensified, consistent with a higher degree of opening of the hairpin-capping units that enhances the opening of the pores by the autonomous nicking/analyte regeneration process. Similarly, at a fixed concentration of the analyte-biomarker, the release of RhB from the pores is controlled by the concentration of the Nb.BbvCI nicking enzyme. FIG. 9(C) shows the fluorescence intensities of the released RhB, upon treatment of the (6)-capped RhB-loaded MP-SiO2 NPs with a constant concentration of the analyte-biomarker, 1 µM, for a fixed time-interval of 60 minutes, in the presence of variable amounts of the nicking enzyme. As the content of the enzyme increases, the amount of released RhB is higher, consistent with the enhanced opening of the pores through the autonomous biocatalytic cleavage of the capping units and the regeneration of 9 the analyte-biomarker. In the presence of 0.5 U/µL of the nicking enzyme, the fluorescence intensity of the system reaches a saturation value, implying that under these conditions most of the RhB was removed from the mesoporous matrix. Control experiments, FIG. 9(D), reveal that when the (6)-capped pores are not interconnected with the nicking enzyme or the analyte-biomarker, the leakage of RhB is observed, curve (a), and the analyte-biomarker or the nicking enzyme alone have little effect on the release of RhB, curves (b) and (c), respectively. FIG. 9(D), curve (d) shows the time-dependent fluorescence spectra of the solution, upon the treatment of the (6)-hairpin-locked MP-SiO2 NPs that include entrapped RhB, with the analyte-biomarker (7), 1 µM, in the presence of the nicking enzyme, 0.5 U/µl. The effective release of RhB from the pores proceeds only when the (6)-hairpin blocked pores are reacted with the analyte-biomarker and the nicking enzyme. A time-controlled release of RhB is observed in curve (d), that tends to reach a saturation value after ca. 60 minutes. From the saturated value of the fluorescence spectrum, and using an appropriate calibration curve, it was estimated that the release amount of RhB is ca. 12.4 µmol/g MP-SiO2 NPs. Further support that the hybridization of (7) to the hairpin-(6)-modified MP-SiO2 NPs leads to a duplex structure being nicked by Nb. BbvCI and the unlocking of the pores through the release of the fragmented capping units was obtained by gel electrophoresis experiments that followed the fragmented product. Also, the opening of the (6)-modified pores by the coupled opening of the hairpins by means of the analyte-biomarker and the autonomous nicking of the capping units, by means of the precise nicking recognition sites (CCTCAGC/GGAGT▲CG), reveals impressive selectivity, FIG. 9(E). One-base, two-base or three-base mismatches in the analyte-biomarker, sequence (8), (9) and (10), respectively, do not open the hairpin structure and the autonomous biocatalytic removal of the capping units by the nicking enzyme is prohibited. Thus, in the presence of the mutants, the release of RhB from the pore is very similar to the intrinsic leakage of the dye from the (6)-functionalized pores, FIG. 9(D), curves (a), (b) and (c), respectively.

In the systems described above, the opening of the nucleic acid-functionalized pores was triggered by nucleic acid analyte-biomarker strands, where biocatalytic reactions, stimulated by Exo III or the nicking enzymes, provided means to remove the capping elements while regenerating the biomarker units. In a further embodiments of the invention the opening of the pores and release the entrapped substrate (RhB) is achieved by means of aptamer-substrate complexes and the coupled autonomous biocatalytic degradation of the aptamer-substrate complex, while regenerating the substrate-biomarker. One configuration for the controlled release of RhB from the MP-Si02 NPs pores by the coupled ATP-aptamer complex and Exo III biocatalytic process is depicted in FIG. 10(A). The nucleic acid (11), substituting the MP-SiO2 NPs, exists at 90° C. in the random coil structure, thus allowing the loading of the pores with RhB. The pores with the entrapped RhB are capped by the hairpin structures that are stabilized at 25° C. The hairpin structures of (11) are designed to include an aptamer sequence (green), and this is conjugated to a single-stranded sequence (pink), which ensures that Exo III can't hydrolytically affect the hairpin structures. In the presence of ATP the hairpin (11) opens, and the 3'-end of the opened hairpin is designed to form a duplex structure with the 5'-domain of (11). That is, the generated ATP-aptamer complex is cooperatively stabilized by this duplex domain. The resulting duplex provides, however, an active site for the Exo III hydrolytic digestion of the 3'-end of the duplex. This biocatalytic process destabilizes the ATP-aptamer complex that releases ATP for a secondary opening of a hairpin structure, that yields the aptamer-ATP complex. Thus, opening of the hairpin by ATP triggers-on the coupled Exo III-stimulated regeneration of ATP for the autonomous biocatalytic "digestion" of the capping units, and the release of the entrapped RhB. FIG. 10(B) depicts the fluorescence spectra of the RhB released from the pores, upon treatment of the MP-SiO2 NPs with different concentrations of ATP, for a fixed time-interval of 90 minutes, and using a constant concentration of Exo III, corresponding to 1 U/µL. Similarly, FIG. 10(C) shows the fluorescence spectra of RhB released from the MP-SiO2 NPs upon treatment of the NPs with different concentrations of Exo III and a constant concentration of ATP (1 mM), for a fixed time-interval of 90 minutes. The release of RhB from the porous material is enhanced either by increasing the concentration of ATP or the concentration of Exo III, consistent with the fact that these two ingredients control the opening of the capping units of the pores. FIG. 10(D) shows a set of control experiments, that were performed to elucidate the functions of ATP and Exo III on the controlled release of RhB from the pores. In the absence of ATP or Exo III, leakage of RhB from the pores is observed, curve (a). In the presence of either ATP or Exo III, a similar leakage rate of RhB is observed, curves (b) and (c), respectively. The enhanced release of RhB is detected only in the presence of ATP, 1 mM, and Exo III, 1 U/µl, curve (d), consistent with the suggested mechanism where the opening of the (11)-functionalized pores, to yield the respective aptamer-substrate complex, is coupled to the autonomous cleavage of the capping units, and the regeneration of the ATP analyte-biomarker. Using the calibration curve it was estimated that the release amount of RhB is ca. 9.3 µmol/g MP-SiO2 NPs Finally, the controlled opening of the (11)-functionalized MP-SiO2 NPs is selective for ATP and other nucleotides (UTP, GTP, CTP) do not affect the opening of the pores, FIG. 10(E).

The coupled nucleic acid/nicking enzyme catalytic opening of the pores, the aptamer-substrate complex/nicking enzyme method was implemented, to drive the autonomous opening of the pores for the controlled release of RhB, FIG. 11(A). The MP-SiO2 NPs were modified with (12) and loaded with RhB at 90° C. Upon cooling of the system to 25° C., the single-strand stabilizes the hairpin structures that cap the RhB in the pores. The stem-region of the hairpin does not include the sequence-specific domain to be nicked by the Nb. BbvCI nicking recognition sites (CCTCAGC/GGAGT▲CG). The formation of the ATP-aptamer complex rearranges the hairpin structure to a new structure, that includes the nicking domain. The fragmentation of the stem region of the ATP-aptamer complex releases a major fragment of the aptamer sequence, resulting in the release of ATP from the fragmented sequence. The recycled ATP biomarker opens all additional hairpin capping units, thus triggering-on the autonomous opening of the pores and the release of RhB, by the cyclic coupled opening of the hairpin units by ATP, formation of the ATP-aptamer complex, the subsequent nicking enzyme stimulated fragmentation (GGAGT▲CG) of the aptamer sequence and the recycling of the ATP biomarker. FIG. 11(B) shows the fluorescence spectra of the released RhB upon the treatment of the (12)-capped RhB-loaded MP-SiO2 NPs, and a constant concentration of the nicking enzyme, 0.5 U/µl, in the presence of variable concentrations of ATP, for a fixed time-interval of 90 minutes. As the concentration of ATP increases the fluorescence intensities of the released RhB are intensified. These results are consistent with the fact that as the concentration of ATP is higher, the autonomous opening of the pores through the concentration of ATP is higher, the coupled formation of the ATP-aptamer complex and its fragmentation by the nicking enzyme is enhanced. FIG.

11(C) shows the fluorescence intensities of the released RhB, upon treatment of the RhB-loaded MP-SiO2 NPs with a fixed concentration of ATP, 1 mM, and variable concentrations of the Nb. BbvCI nicking enzyme, for a fixed time-interval of 90 minutes. As the concentration of the nicking enzyme increases, the release of RhB is higher, consistent with the enhanced opening of the pores. FIG. 11(D) shows the time-dependent fluorescence changes 13 upon the release of RhB, by the coupled ATP/nicking enzyme opening of the pores, in comparison to control systems. While the (12)-modified MP-SiO2 NPs reveal an intrinsic leakage of RhB, curve (a), the leakage process in the presence of only ATP or the nicking enzyme is only slightly effected, curves (b) and (c), respectively. Only the combination of ATP, 1 mM, and the Nb. BbvCI nicking enzyme, 0.5 U/μl, as a substantial enhancement in the release of RhB, curve (d), are consistent with the suggested mechanism. Using the calibration curve it was estimated that the release amount of RhB is ca. 14.1 μmol/g MP-SiO2 NPs. FIG. 11(E) reveals the selective ATP-triggered release of RhB from the (12)-functionalized MP-SiO2 NPs, using the respective ATP-aptamer complex and the nicking enzyme as biocatalyst. The release of RhB in the presence of the nucleotides CTP, UTP and GTP the release of RhB is very similar to the intrinsic leakage of RhB from the MP-SiO2 NPs that is observed in the absence of ATP/nicking enzyme, FIG. 11D, curves (a), (b) and (c) as compared to (d).

This embodiment was further extended by demonstrating that the nucleic acid-triggered or ATP-triggered release of the anti-cancer drug camptothecin, CPT, can be stimulated by the exonuclease III or the nicking enzyme, Nb. BboCI, mediated unlocking of the pores. Furthermore, the effective intracellular release of CPT in breast cancer cells is described, and the effectiveness of unlocking pores and releasing CPT in breast cancer cells and normal breast cells and the effect on cell death in these cells were compared. FIG. 12(A) shows the fluorescence intensities of the released CPT, upon the treatment of CPT-(1)-lock MP-SiO2 NPs with different concentrations of the target DNA, (2), in the presence of Exo III for a fixed time-interval of 60 minutes. As the concentration of the target DNA increases, the fluorescence is intensified, implying that more CPT was released from the pores. FIG. 12(B) depicts the time-dependent fluorescence change upon releasing CPT from the (1)-locked MP-SiO2 NPs. The respective control experiments are shown in FIG. 12(B), curves (a)-(c). Evidently, effective release of CPT is observed only upon unlocking of the pores with (2) and the Exo III degradation of the locking sites, curve (d). Similar results are observed upon releasing CPT from the (6)-locked MP-SiO2-NPs using the target DNA (7) and the nicking enzyme Nb. BbvCI, as opening mechanism, FIGS. 12(C) and (D). In analogy, the ATP-stimulated opening and the release of CTP from the pores in the presence of Exo III or the nicking enzyme were studied. FIG. 13(A) shows the fluorescence spectra observed upon the treatment of (11)-capped MP-SiO2 NPs that include in-pore trapped CPT with different concentrations of ATP and Exo III, for a fixed time-interval of 90 minutes. As the concentration of ATP increases, the amount of CPT released is higher, consistent with the enhanced release of CPT from the pores. Using the appropriate calibration curve, it was estimated that ca. 10.8 μmol/g MP-SiO2 NPs of CPT are released, after a time-interval of 90 minutes. FIG. 13(B) depicts the time-dependant fluorescence change upon releasing CPT from the (11)-capped MP-SiO2 NPs. Similarly, FIGS. 13(C) and (D) show the release of CPT from the (12)-locked pores of the MP-SiO2 NPs, using ATP as modifier of the "locker-keys" through the formation of the respective ATP-aptamer capping units, and the opening of the pores by the nicking-enzyme degradation of the ATP-aptamer complexes. As the concentration of the ATP increases, the release of CPT is enhanced, consistent with the increase in the content of the aptamer-ATP complexes, and their digestion by the nicking enzyme, Nb. BbvCI. The rate of release of the CPT from the pores in the respective control experiments, FIG. 13(D), curves (a)-(c), and in the presence of the nicking enzyme, FIG. 13(D), curve (d), indicate that the CPT trapped in the (12)-locked pores is effectively released only in the presence of the biomarker and the nicking enzyme. From the respective calibration curve, it was estimated that ca. 13.4 μmol/g MP-SiO2 NPs were released from the pores after a time-interval of ca. 90 minutes.

The concept to unlock and release CPT from the pores of the MP-SiO2 NPs by transforming the "locker-keys" with DNA or ATP biomarkers into new functional units that are unlocked by biocatalytic processes (Exo III or Nb. BbvCI), was formulated as a general approach to control drug delivery and regulate cell death. Specifically, the high metabolism in cancer cells leads to high contents of ATP and thus it might provide a chemical trigger for the selective opening of the pores in cancer cells. The enhanced release of the chemotherapic drug, CPT, in the cancer cells as then anticipated to induce the superior death of cancer cells as compared to normal cells.

The possible ATP-triggered release of CPT from the (11)-locked MP-SiO2 NPs was examined and the effect that the released CPT has on the death of the respective cells. In the first step, the possible cytotoxicity of the MP-SiO2 NPs on cells was examined. The exterior surface of the DNA-locked NPs was functionalized with fluorescein isothiocyanate (FTIC) and MDA-MB-231 (breast cancer cells), MCF-10a (normal breast cells) cells were subjected to the fluoresceine-labeled NPs. Rapid endocytosis into the cells was observed, yet no cytotoxic effect was detected. In the next step, we made use of the fact that EndoGI is present in cancer cells and it exhibits Exo III-type exonuclease activity. The MP-SiO2 NPs were loaded with CPT and locked the drug in the pores with the ATP-sensitive hairpin (11). MDA-MB-231 breast cancer cells and MCF-10a normal breast cells were subjected to the CPT-loaded MP-SiO2 NPs. FIG. 14 shows the fluorescence feature of the MDA-MB-231 cells, and the viability of the two types of cells after 48 hours of treatment with the MP-SiO2 NPs. FIG. 14(A) shows the time-dependent fluorescence features of the MDA-MB-231 cells treated with the CPT loaded NPs. The cells reveal already after 24 hours green fluorescence, corresponding to the fluorescein labels associated with the NPs, and this fluorescence prevails even after 48 hours. This implies that the NPs are incorporated in the cells. The blue fluorescence, corresponding to unlocked CPT, is not observed after 24 hours, reveals weak fluorescence after 30 hours and this fluorescence is intensified after a time-interval of 48 hours, implying that after this time-interval CPT was released into the cells. FIG. 14(B) panels I and II summarize the effect of the CPT-loaded NPs on the viability of the cells (Panel I—MDA-MB-231 breast cancer cells, Panel II—MCF-10a normal breast cells). Appropriate control systems are provided. From the results one may realize that ca. 65% of the cancer cells revealed cell death after 48 hours, as compared to the CPT-non-treated control (entry (a) vs. (b)), while only 25% of non-cancerous cells experienced cell-death after this time interval (48 hours). In a further control experiment, the two cell cultures were subjected to oligomycin, upon treatment with the CPT-loaded MP-SiO2 NPs. Oligomycin acts as a suppressor of the ATPase synthesis of ATP43, and hence, the ATP-stimulated release of CPT in the cancer cells should be suppressed in the presence of oligomycin. Indeed, FIG. 14(B), panel I (compare entries (b) to (d)) reveals that in the presence of oligomycin only a 50% cell death was observed as compared to 65% in the absence of the ATP synthesizing suppressor. These results are consistent with the fact that the high metabolic synthesis of ATP in the cancer cells leads to enhanced opening of the MP-SiO2 NPs, and to the effective release of CPT that affects the cell death.

EXAMPLE I

—SiO2 Nanoparticles for the DNAzyme-Induced Multiplexed Release of Substrates

Materials

Tetraethyl orthosilicate (TEOS), (3-aminopropyl) triethoxysilane (APTES) and 2,6-pyridinedicarboxylic acid (PDCA) were purchased from Aldrich. N-(ε-maleimidocaproyloxy) sulfosuccinimide ester (Sulfo-EMCS) was purchased from Pierce Biotechnologies. Hexadecyltrimethylammonium bromide (CTAB), methylene blue (MB+), thionine (Th+), doxorubicin hydrochloride, 4-(2-Hydroxyethyl)piperazine-1-ethanesulfonic acid sodium salt (HEPES), magnesium (II) chloride, zinc (II) acetate dihydrate, lead (II) acetate trihydrate, calcium (II) acetate hydrate, strontium (II) chloride hexahydrate, barium (II) carbonate, copper (II) chloride, cobalt (II) acetate tetrahydrate, manganese (II) carbonate, nickel (II) acetate tetrahydrate, ferrous (II) sulfate heptahydrate and mercury (II) acetate were all purchased from Sigma. Ultrapure water from a NANOpure Diamond (Barnstead Int., Dubuque, Iowa) source was used throughout the experiments. All DNA oligonucleotide sequences were purchased from Integrated DNA Technologies Inc. (Coralville, Iowa). After diluting The thiol labeled RNA sequence (1) with HEPES buffer (20 mM, pH 7.0) solution, it was reduced by 0.1 M of dithiothreitol (DTT), and stored at −20° C., then purified with Illustra™ MicroSpin™ G-25 Columns (GE Healthcare) before use.

The following nucleic acids were used:

(1)
(SEQ. NO. 1)
5'-SH(CH2)6CAACAACATrAGGACATAGAAGAAGAAG-3'

(4)
(SEQ. NO. 2)
5'-CTTCTTCTTCTATGTCAGCGATCCGGAACGGCACCCATGTTGTTGT
T-G-3'

(5)
(SEQ. NO. 3)
5'-CTTCTTCTTCTATGTCTCCGAGCCGGTCGAAATGTTGTTG-3'

(6)
(SEQ. NO. 4)
5'-CTTCTTCTTCTATGTCAGCGATCCTGGGGAGTATTGCGGAGGAAG-
GCACCCATGTTGTTGTTG-3'

(7)
(SEQ. NO. 5)
5'-CTTCTTCTTCTATGTCAGCGATCTTTTCGGAAACGTTTAGCACCCA
T-GTTGTTGTTG-3'

(8)
(SEQ. NO. 6)
5'-CTTCTTCTTCTATGTCTCATGGGGGAGTATTGCGGAGGAAGGTCGAA
ATGTTGTTG-3'

Instrumentation

Fluorescence measurements were performed using a Cary Eclipse device (Varian Inc.). The excitation wavelengths of MB+, Th+ and doxorubicin dyes were 663 nm, 600 nm and 494 nm, respectively. UV-vis absorption spectra were recorded using a Shimadzu UV-2401 spectrophotometer. SEM images were taken by a Magellan 400L scanning electron microscope.

Synthesis of Mesoporous Silica Nanoparticles

Amino-functionalized mesoporous SiO2 NPs were prepared according to Chen, C.; Pu, F.; Huang, Z.; Ren, J.; Qu, X. Nucleic Acid Res. 2011, 39, 1638. The resulting NPs were precipitated, washed with distilled water and methanol, and were dried in air. In order to remove the N-cetyltrimethylammonium bromide (CTAB), the SiO2 NPs were refluxed for 16 h in a solution composed of HCl (37%, 1 mL) and methanol (80 mL), and were, then, extensively washed with distilled water and methanol. The resulting, CTAB-free, amino-functionalized mesoporous SiO2 NPs were stored in vacuum to remove the remaining solvent from the pores.

Loading of the Dyes

Monodispersed SiO2 NPs were prepared as follows: 10 mg silica NPs were immersed in 950 μL of HEPES buffer (20 mM, pH 7.0) and were sonicated for 30 min. The solution was reacted with 50 μL of sulfo-EMCS (10 mg/mL) and the resulting mixture was shaken for 30 min. To remove the excess EMCS, the mesoporous SiO2 NPs were precipitated using centrifugation at 10000 rpm for 3 min, and redissolved in 950 μL of HEPES buffer (20 mM, pH 7.0). The purified SiO2 NPs were reacted with 50 μL of the thiolated oligonucleotide ((1), 1 mM), and the resulting solution was shaken for 2 hours. Following the modification, the excess of DNA was removed by precipitation of the silica NPs as described before. The quantification of left RNA was accomplished by UV-vis spectroscopy to be 38 nmol, which corresponded to 1.2 μmol/g SiO2 NPs. The purified particles were then dissolved in 900 μL of HEPES buffer (20 mM, pH 7.0), containing 500 mM NaCl, to which 100 μL of dye (1 mM MB+, Th+ or doxorubicin) was added, and the resulting solution was shaken overnight. Following the loading of the dye, the solution was incubated with 50 μL of complementary DNAs (1 mM of DNA (4), (5), (6), (7) or (8), respectively) and the resulting mixture was shaken for 2 h. The DNA-capped mesoporous SiO2 NPs obtained by this procedure were washed eight times using HEPES buffer (20 mM, pH 7.0), containing 500 mM NaCl until a low background was achieved, to remove any physically adsorbed dye from the surface of the SiO2 particles. The washing steps were monitored via the absorption spectrum of the dye during the process. The loading amount of MB+ or Th+ in the Mg2+- or Zn2+-dependant DNAzyme-modified SiO2 NPs was roughly calculated to be 6.3 μmol/g or 7.5 μmol/g SiO2 NPs, respectively.

Release of the Dyes

To monitor the release process of the dye from the mesoporous SiO2 NPs in the presence of the Mg2+- or Zn2+-ions, the particles were suspended in 1 mL HEPES buffer (20 mM, pH 7.0), containing 500 mM NaCl, and divided into five 190 μL aliquots. To these samples, the different ions at variable concentrations were added and shaken for 1 hour or 40 minutes for Mg2+ or Zn2+, respectively. The fluorescence spectra of the samples were recorded after precipitation. To test the release process of the dye in the ATP- or Hg2+-stimulated DNAzyme-dependant SiO2 NPs, the mesoporous SiO2 NPs were dissolved in 1 mL HEPES buffer (20 mM, pH 7.0), containing 500 mM NaCl and 20 mM Mg2+ or 10 mM Zn2+, which were divided into five 190 µL samples. The SiO2 NPs were then reacted with 10 µL of ATP (2 mM), or Hg2+ ions (20 µM). The resulting solutions were shaken for 90 minutes or 1 hour for ATP or Hg2+ ions, respectively. This was followed by measuring the fluorescence spectra of the samples after precipitation of the SiO2 NPs.

EXAMPLE II

—Amplified Biocatalytic Release of Substrates from Nucleic Acids-Capped Mesoporous SiO2 Using DNA or Molecular Biomarkers as Triggering Stimuli Materials Tetraethyl orthosilicate (TEOS), (3-aminopropyl) triethoxysilane (APTES) and rhodamine B (RhB) were purchased from Aldrich. N-(ε-Maleimidocaproyloxy) sulfosuccinimide ester (Sulfo-EMCS) was purchased from Pierce Biotechnologies. Hexadecyltrimethylammonium bromide (CTAB) and 4-(2-Hydroxyethyl)piperazine-1-ethanesulfonic acid sodium salt (HEPES) were purchased from Sigma. Exonuclease III (Exo III), NEBuffer 1, nicking enzyme Nb. BbvCI and NEBuffer 2 were purchased from New England Biolabs. Camptothecin (CPT), oligomycin, adenosine 5'-triphosphate (ATP), uridine 5'-triphosphate (UTP), cytidine 5'-triphosphate (CTP) and guanosine 5'-triphosphate (GTP) were purchased from Sigma-Aldrich. All other chemicals used were of analytical grade and were used as received without any further purification. Ultrapure water from a NANOpure Diamond (Barnstead Int., Dubuque, Iowa) source was used throughout the experiments. All the DNA oligonucleotide sequences were purchased from Integrated DNA Technologies Inc. (Coralville, Iowa). The oligonucleotides were used as provided and diluted in aqueous solution.

The recognition site of the Nb. BbvCI nicking enzyme is as follow.

```
5' . . . CCTCAGC . . . 3'

3' . . . GGAGT▲CG . . . 3'
```

The sequences of the oligomers are as follows:

(1)
Tm = 67.3° C.
(SEQ. NO. 7)
5'-SH(CH2)6 CAA GGG CAG AAG TCT TCA CTG CCC TTG CAC ACT-3'

(2)
(SEQ. NO. 8)
5'-AGT GTG CAA GGG CAG TGA AGA CTT GAT TGT-3'

(3)
(SEQ. NO. 9)
5'-AGT GTG CAA GAG CAG TGA AGA CTT GAT TGT-3'

(4)
(SEQ. NO. 10)
5'-AGT GTG CTA GAG CAG TGA AGA CTT GAT TGT-3'

(5)
(SEQ. NO. 11)
5'-AGT GTG CTA GAG CAG TTA AGA CTT GAT TGT-3'

(6)
Tm = 58.9° C.
(SEQ. NO. 12)
5'-SH(CH2)6AACGAAGCTGAGGATGTGTTCGTT-3'

(7)
(SEQ. NO. 13)
5'-ATCCTCAGCTTCG-3'

(8)
(SEQ. NO. 14)
5'-ATCCTGAGCTTCG-3'

(9)
(SEQ. NO. 15)
5'-ATCATGAGCTTCG-3'

(10)
(SEQ. NO. 16)
5'-ATCATGAGCGTCG-3'

(11)
Tm = 69.8° C.
(SEQ. NO. 17)
5'-SH(CH2)6CCTCCGCTACCTGGGGGAGTATTGCGGAGGAAGGTA-3'

(12)
Tm = 74.9° C.
(SEQ. NO. 18)
5'-SH(CH2)6CCTCCGCAATACTCCGCTGAGGCCTGGGGGAGTATTGCG GAGGAAGGCCTCAGC-3'

Instruments

Fluorescence emission measurements were performed using a Cary Eclipse Device (Varian Inc.). Rhodamine B (RhB) was excited at a wavelength of 554 nm. UV-vis absorption spectra were recorded with a Shimadzu UV-2401 spectrophotometer. TEM images were recorded on a Tecnai F20 G2 (FEI Co.) using an accelerating voltage of 200 kV. Surface areas were determined using a Nova 1200e BET meter (Quantachrome Instruments, USA) by nitrogen adsorption/desorption at the temperature of liquid nitrogen.

Synthesis of Mesoporous Silica Nanoparticles (MP-SiO2 NPs)

Amino-functionalized MP-SiO2 NPs were prepared according to a previously reported procedure.30 The collected SiO2 NPs were washed with large volumes of distilled water and ethanol using centrifuge at 8000 rpm for 3 min. To remove N-cetyltrimethylammonium bromide (CTAB), the SiO2 NPs were refluxed for 16 h in a solution composed of HCl (37%, 1.00 ml) and ethanol (80.00 ml). The obtained NPs were extensively washed with distilled water and ethanol. Finally, to remove the remaining solvent from the pores, the resulting, CTAB-free, amino-functionalized MP-SiO2 NPs were placed in vacuum at 75° C. for 12 h.

Loading of the Dye and Capping of the Pores

To prepare monodispersed MP-SiO2 NPs solution, 10 mg of silica NPs were placed into 950 µl of HEPES buffer (20 mM, pH 7.0) and sonicated for 30 min. The solution was reacted with 50 µl of sulfo-EMCS (10 mg/ml) and the mixture was mixed for 30 min. To remove excess of EMCS, the MP-SiO2 NPs were collected using centrifuge at 8000 rpm for 3 min, and redissolved in 950 µl of HEPES buffer (20 mM, pH 7.0). The purified SiO2 NPs were reacted with the freshly reduced and purified thiolated oligonucleotides (1), (6), (11), (12) (80 μl, 1 mM), and the resulting solution was mixed for 2 h, the excess DNA was removed from the NPs solution by precipitation. The quantification of left excess DNA was accomplished by UV-vis spectroscopy in DNA/Exo III or DNA/nicking enzyme system to be 61 nmol or 58 nmol, which corresponded to an amount of DNA immobilized to be 1.9 μmol/g or 2.2 μmol/g SiO2 NPs, respectively.

A water bath was used (90° C.) for the loading of the dye to the pores, in order to open the hairpin structure of the linked DNA. The purified MP-SiO2 NPs were dissolved in 900 μl of HEPES buffer (20 mM, pH 7.0, containing 50 mM NaCl), 100 μl of RhB or CPT (10 mM) was added into the solution, and the reaction mixture was heated to 90° C. or 75° C., respectively, using a water bath for 2 h under continuous stirring. Then, the sample was immersed separately in water bath at 75° C., 50° C. and 25° C. for 20 min under continuous stirring during the annealing process Finally, the MP-SiO2 NPs were washed at least seven times using distilled water, until a low background was achieved, to remove the physically adsorbed dye from the surface of the SiO2 particles. The loading amount of RhB in DNA/Exo III or DNA/nicking enzyme systems was roughly calculated to be 37.8 μmol/g or 31.3 μmol/g SiO2 NPs, respectively. The loading amount of CPT in DNA/Exo III or DNA/nicking enzyme systems was calculated to be 34.5 μmol/g or 28.6 μmol/g SiO2 NPs, respectively.

Release of the Dye

In order to monitor the release of the dye in the two different systems, DNA/Exo III or DNA/nicking enzyme, the above mentioned MP-SiO2 NPs were suspended in 850 μl of distilled water, and divided into five samples, each containing 160 μl of solution. Then, 20 μl of buffer 1 and 10 μl different concentration of Exo III, or 20 μl of buffer 2 and 10 μl different concentration of nicking enzyme were added into the resulting solution, respectively, and shaked gently. Finally, 10 μl different concentrations of DNA were added into the mixture and shaked for 1 h, and then emitted fluorescence spectra of the samples were measured after precipitation.

In order to test the release of the dye in the ATP stimulated Exo III or nicking enzyme system, the washed MP-SiO2 NPs were dissolved in 850 μl of distilled water, and divided into five samples, 160 μl each. The SiO2 NPs were incubated with 20 μl of buffer 1 and 10 μl different concentration of Exo III, or 20 μl of buffer 2 and 10 μl different concentration of nicking enzyme, respectively. Then, 10 μl different concentrations of ATP were added, the obtained solutions were shaken for 90 min, and then the fluorescence spectra were measured after precipitation.

Effect of CPT on the Death of MDA-MB-231 (Breast Cancer Cells), and MCF-10a (Normal Breast Cells) Cells MDA-MB-231 (breast cancer cells), MCF-10a (normal breast cells) cells were planted at a density of 27000 cells per well of 24-well tissue culture plates. After overnight, cells were pre-incubated with oligomycin (25 μg/ml) for 1 h before, then loaded with MP-SiO2 (150 μg/ml) for two times (each loading lasted 3 h). Between the loadings cells were washed with fresh growth medium and then reloaded. Cells were further incubated overnight. To determine cell viability, 10 μl of Alamar blue solution was added to each well of the plate and the cells were incubated in the CO2 incubator for an additional 1 h. The fluorescence of Alamar blue was checked in plate-reader (TECAN). Cells were cultured in glass-bottom microscope dishes and analyzed by epi-fluorescence microscope, aided by confocal (quality equivalent) opti-grid device (Nikon TE 2000 microscope equipped with a thermostated stage and a Hamamatsu Orca-Era CCD camera) and driven by a Volocity 4 operating system (Improvision, Coventry, UK) that was used for both image data acquisition and analysis. Uptake of the NPs and release of CPT from the particles were measured microscopically with FITC-labeled (ex: 519 nm) and CPT-loaded (ex: 423 nm) NPs.

The invention claimed is:

1. A porous substrate comprising pores and at least one active agent entrapped within the pores of said porous substrate;
   at least one capping nucleic acid sequence in a locked conformation capping said pores and entrapping said at least one active agent within said pores;
   said capping nucleic acid sequence, upon association with at least one first analyte changes conformation to form a cleavage-prone conformation, is capable of being cleaved by a biocatalyst thereby allowing the release of said entrapped at least one active agent.

2. A porous substrate according to claim 1, wherein said pores are capped by at least two independent capping nucleic acid sequences.

3. A porous substrate according to claim 1, wherein said capping nucleic acid sequence is either single or double stranded.

4. A porous substrate according to claim 1, wherein said capping nucleic acid sequence comprises a DNAzyme sequence.

5. A porous substrate according to claim 1, wherein said capping nucleic acid sequence comprises a DNAzyme sequence; said DNAzyme sequence being enlarged with foreign nucleotide domain having a free conformation and an active conformation upon associating with at least one second analyte, said active conformation of said DNAzyme sequence capable of being cleaved upon association with said at least one first analyte, thereby allowing the release of said entrapped at least one active agent.

6. A porous substrate according to claim 1, wherein said at least one capping nucleic acid sequence is a hairpin loop sequence.

7. A porous substrate according to claim 1, wherein said pores are capped by at least two independent capping nucleic acid sequences, said at least two independent capping nucleic acid sequences being at least two independent hairpin loop sequences.

8. A porous substrate according to claim 1, wherein said at least one capping nucleic acid sequence is a hairpin loop sequence capable of being cleaved upon association with at least one analyte nucleic acid strand.

9. A porous substrate according to claim 1, wherein said at least one capping nucleic acid sequence is a hairpin loop sequence capable of being cleaved upon association with at least one analyte nucleic acid strand, said at least one analyte nucleic acid strand being a biomarker for at least one ailment or condition.

10. A porous substrate according to claim 1, wherein said at least one capping nucleic acid sequence is a hairpin loop sequence comprising a nucleotide domain that is capable of being cleaved upon association with at least one analyte.

11. A porous substrate according to claim 1, wherein said at least one capping nucleic acid sequence is a hairpin loop sequence comprising a nucleotide domain having a free conformation and an active conformation upon associating with at least one second analyte.

12. A porous substrate according to claim 1, wherein said capping sequence comprises a nicking enzyme specific nucleotide.

13. A porous substrate according to claim 1, wherein said biocatalyst capable of cleaving said capping nucleic acid sequence is an exonuclease or an endonuclease.

14. A porous substrate according to claim 1, wherein said biocatalyst capable of cleaving said capping nucleic acid sequence is a nicking enzyme.

15. A porous substrate according to claim 1, wherein said porous substrate is a semi-metal oxide nano-particle.

16. A porous substrate according to claim 1, wherein said porous substrate is a mesoporous silica nano-particle.

\* \* \* \* \*

SEQUENCE LISTING

```
<160> NUMBER OF SEQ ID NOS: 18

<210> SEQ ID NO 1
<211> LENGTH: 28
<212> TYPE: DNA
<213> ORGANISM: Artificial Sequence
<220> FEATURE:
<223> OTHER INFORMATION: thiolated oligonucleotide
<220> FEATURE:
<221> NAME/KEY: misc_feature
<222> LOCATION: (1)..(1)
<223> OTHER INFORMATION: n is equal to SH(CH2)6
<220> FEATURE:
<221> NAME/KEY: misc_feature
<222> LOCATION: (11)..(11)
<223> OTHER INFORMATION: n is equal to adenine ribonucleotide

<400> SEQUENCE: 1
ncaacaacat nggacataga agaagaag                                        28

<210> SEQ ID NO 2
<211> LENGTH: 48
<212> TYPE: DNA
<213> ORGANISM: Artificial Sequence
<220> FEATURE:
<223> OTHER INFORMATION: complementary DNA

<400> SEQUENCE: 2
```
cttcttcttc tatgtcagcg atccggaacg gcacccatgt tgttgttg          48

<210> SEQ ID NO 3
<211> LENGTH: 40
<212> TYPE: DNA
<213> ORGANISM: Artificial Sequence
<220> FEATURE:
<223> OTHER INFORMATION: complementary DNA

<400> SEQUENCE: 3
cttcttcttc tatgtctccg agccggtcga aatgttgttg                   40

<210> SEQ ID NO 4
<211> LENGTH: 64
<212> TYPE: DNA
<213> ORGANISM: Artificial Sequence
<220> FEATURE:
<223> OTHER INFORMATION: complementary DNA

<400> SEQUENCE: 4
cttcttcttc tatgtcagcg atcctggggg agtattgcgg aggaaggcac ccatgttgtt  60
gttg                                                          64

<210> SEQ ID NO 5
<211> LENGTH: 57
<212> TYPE: DNA
<213> ORGANISM: Artificial Sequence
<220> FEATURE:
<223> OTHER INFORMATION: complementary DNA

<400> SEQUENCE: 5
cttcttcttc tatgtcagcg atcttttcgg aaacgtttag cacccatgtt gttgttg    57

<210> SEQ ID NO 6
<211> LENGTH: 56
<212> TYPE: DNA
<213> ORGANISM: Artificial Sequence
<220> FEATURE:
<223> OTHER INFORMATION: complementary DNA

<400> SEQUENCE: 6
cttcttcttc tatgtctcat gggggagtat tgcggaggaa ggtcgaaatg ttgttg     56

<210> SEQ ID NO 7
<211> LENGTH: 34
<212> TYPE: DNA
<213> ORGANISM: Artificial Sequence
<220> FEATURE:
<223> OTHER INFORMATION: thiolated oligonucleotides
<220> FEATURE:
<221> NAME/KEY: misc_feature
<222> LOCATION: (1)..(1)
<223> OTHER INFORMATION: n is equal to SH(CH2)6

<400> SEQUENCE: 7
ncaagggcag aagtcttcac tgcccttgca cact                         34

<210> SEQ ID NO 8
<211> LENGTH: 30
<212> TYPE: DNA
<213> ORGANISM: Artificial Sequence
<220> FEATURE:
<223> OTHER INFORMATION: hairpin loop sequence

<400> SEQUENCE: 8
agtgtgcaag ggcagtgaag acttgattgt                                30

<210> SEQ ID NO 9
<211> LENGTH: 30
<212> TYPE: DNA
<213> ORGANISM: Artificial Sequence
<220> FEATURE:
<223> OTHER INFORMATION: hairpin loop sequence

<400> SEQUENCE: 9
agtgtgcaag agcagtgaag acttgattgt                                30

<210> SEQ ID NO 10
<211> LENGTH: 30
<212> TYPE: DNA
<213> ORGANISM: Artificial Sequence
<220> FEATURE:
<223> OTHER INFORMATION: hairpin loop sequence

<400> SEQUENCE: 10
agtgtgctag agcagtgaag acttgattgt                                30

<210> SEQ ID NO 11
<211> LENGTH: 30
<212> TYPE: DNA
<213> ORGANISM: Artificial Sequence
<220> FEATURE:
<223> OTHER INFORMATION: hairpin loop sequence

<400> SEQUENCE: 11
agtgtgctag agcagttaag acttgattgt                                30

<210> SEQ ID NO 12
<211> LENGTH: 25
<212> TYPE: DNA
<213> ORGANISM: Artificial Sequence
<220> FEATURE:
<223> OTHER INFORMATION: thiolated oligonucleotides
<220> FEATURE:
<221> NAME/KEY: misc_feature
<222> LOCATION: (1)..(1)
<223> OTHER INFORMATION: n is equal to SH(CH2)6

<400> SEQUENCE: 12
naacgaagct gaggatgtgt tcgtt                                     25

<210> SEQ ID NO 13
<211> LENGTH: 13
<212> TYPE: DNA
<213> ORGANISM: Artificial Sequence
<220> FEATURE:
<223> OTHER INFORMATION: hairpin loop sequence

<400> SEQUENCE: 13
atcctcagct tcg                                                  13

<210> SEQ ID NO 14
<211> LENGTH: 13
<212> TYPE: DNA
<213> ORGANISM: Artificial Sequence
<220> FEATURE:
<223> OTHER INFORMATION: hairpin loop sequence

<400> SEQUENCE: 14
atcctgagct tcg                                                  13

```
<210> SEQ ID NO 15
<211> LENGTH: 13
<212> TYPE: DNA
<213> ORGANISM: Artificial Sequence
<220> FEATURE:
<223> OTHER INFORMATION: hairpin loop sequence

<400> SEQUENCE: 15
atcatgagct tcg                                                            13

<210> SEQ ID NO 16
<211> LENGTH: 13
<212> TYPE: DNA
<213> ORGANISM: Artificial Sequence
<220> FEATURE:
<223> OTHER INFORMATION: hairpin loop sequence

<400> SEQUENCE: 16
atcatgagcg tcg                                                            13

<210> SEQ ID NO 17
<211> LENGTH: 37
<212> TYPE: DNA
<213> ORGANISM: Artificial Sequence
<220> FEATURE:
<223> OTHER INFORMATION: thiolated oligonucleotides
<220> FEATURE:
<221> NAME/KEY: misc_feature
<222> LOCATION: (1)..(1)
<223> OTHER INFORMATION: n is equal to SH(CH2)6

<400> SEQUENCE: 17
ncctccgcta cctgggggag tattgcggag gaaggta                                  37

<210> SEQ ID NO 18
<211> LENGTH: 55
<212> TYPE: DNA
<213> ORGANISM: Artificial Sequence
<220> FEATURE:
<223> OTHER INFORMATION: thiolated oligonucleotides
<220> FEATURE:
<221> NAME/KEY: misc_feature
<222> LOCATION: (1)..(1)
<223> OTHER INFORMATION: n is equal to SH(CH2)6

<400> SEQUENCE: 18
ncctccgcaa tactccgctg aggcctgggg gagtattgcg gaggaaggcc tcagc              55
```